United States Patent
Yang et al.

(10) Patent No.: US 9,695,421 B2
(45) Date of Patent: Jul. 4, 2017

(54) DENGUE VIRUS-SPECIFIC SIRNA, DOUBLE HELIX OLIGO-RNA STRUCTURE COMPRISING SIRNA, AND COMPOSITION FOR SUPPRESSING PROLIFERATION OF DENGUE VIRUS COMPRISING RNA STRUCTURE

(71) Applicant: BIONEER CORPORATION, Daejeon (KR)

(72) Inventors: Joo Sung Yang, Seoul (KR); Woo Seok Kim, Daejeon (KR); Soon Ja Choi, Daejeon (KR); Han Oh Park, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 0 days.

(21) Appl. No.: 14/902,564

(22) PCT Filed: Jul. 4, 2014

(86) PCT No.: PCT/KR2014/006032
§ 371 (c)(1),
(2) Date: Jan. 1, 2016

(87) PCT Pub. No.: WO2015/002512
PCT Pub. Date: Jan. 8, 2015

(65) Prior Publication Data
US 2016/0145622 A1    May 26, 2016

(30) Foreign Application Priority Data
Jul. 5, 2013    (KR) .......................... 10-2013-0079310

(51) Int. Cl.
*A61K 48/00*    (2006.01)
*C07H 21/02*    (2006.01)
*C07H 21/04*    (2006.01)
*C12N 15/113*    (2010.01)

(52) U.S. Cl.
CPC ...... *C12N 15/1131* (2013.01); *C12N 2310/14* (2013.01); *C12N 2310/315* (2013.01); *C12N 2310/321* (2013.01); *C12N 2310/322* (2013.01); *C12N 2310/351* (2013.01); *C12N 2310/3515* (2013.01); *C12N 2310/3521* (2013.01); *C12N 2310/3525* (2013.01); *C12N 2310/3533* (2013.01)

(58) Field of Classification Search
CPC .......................... C12N 15/113; C12N 2310/11
See application file for complete search history.

(56) References Cited

U.S. PATENT DOCUMENTS

| 5,660,985 | A | 8/1997 | Pieken et al. |
|---|---|---|---|
| 5,753,263 | A | 5/1998 | Lishko et al. |
| 5,808,023 | A | 9/1998 | Sanghvi et al. |
| 5,958,691 | A | 9/1999 | Pieken et al. |
| 6,175,001 | B1 | 1/2001 | Barbas et al. |
| 6,326,358 | B1 | 12/2001 | Manoharan |
| 6,531,584 | B1 | 3/2003 | Cook et al. |
| 7,641,909 | B2 | 1/2010 | Kinney et al. |
| 7,795,417 | B2 | 9/2010 | Burde et al. |
| 7,807,801 | B2 | 10/2010 | Iversen et al. |
| 2003/0224353 | A1* | 12/2003 | Stein .................. C12N 15/1131 435/5 |
| 2006/0078624 | A1 | 4/2006 | Zalipsky et al. |
| 2006/0166919 | A1 | 7/2006 | Shepard et al. |
| 2008/0153737 | A1 | 6/2008 | Lieberman et al. |
| 2008/0227727 | A1 | 9/2008 | Erez et al. |
| 2009/0047338 | A1* | 2/2009 | Swamy .............. C12N 15/1131 424/450 |
| 2011/0206617 | A1* | 8/2011 | Roy ..................... A61K 9/0034 424/9.6 |

(Continued)

FOREIGN PATENT DOCUMENTS

| CA | 2761749 A1 | 11/2010 |
|---|---|---|
| JP | 2013102767 A | 5/2013 |

(Continued)

OTHER PUBLICATIONS

Bertrand et al. (Biochemical and Biophysical Research Communications, 296, 2002, 1000-1004).*
Kim, S., et al., "Folate receptor targeted delivery of polyelectrolyte complex micelles prepared from ODN-PEG-folate conjugate and cationic lipids", "Biotechnol. Prog.", Nov. 15, 2006, pp. 232-237, vol. 23, No. 1.
Akhtar, S., et al., "Nonviral delivery of synthetic siRNAs in vivo", The Journal of Clinical Investigation, Dec. 2007, pp. 3623-3632, vol. 117, No. 12.

(Continued)

*Primary Examiner* — Amy Bowman
(74) *Attorney, Agent, or Firm* — Hultquist, PLLC; Steven J. Hultquist

(57) ABSTRACT

The present invention relates to a dengue virus-specific siRNA, a double-stranded oligo RNA structure comprising the siRNA, and a composition for inhibiting dengue virus replication, which comprises the same, in which the double-stranded oligo RNA structure comprises a hydrophilic compound and hydrophobic compound conjugated to both ends of the double-stranded RNA (siRNA) by a single covalent bond or a linker-mediated covalent bond so that they will be efficiently delivered into cells, and can be converted into nanoparticles by hydrophobic interactions between the double-stranded oligo RNA structures in an aqueous solution. The siRNA included in the double-stranded oligo RNA structure acts specifically on all dengue virus serotypes. The present invention also relates to a method for preparing the double-stranded oligo RNA structure, and a pharmaceutical composition for preventing or treating dengue virus infection, which comprises the double-stranded oligo RNA structure.

21 Claims, 19 Drawing Sheets

(56) References Cited

U.S. PATENT DOCUMENTS

| | | | |
|---|---|---|---|
| 2012/0108803 A1 | 5/2012 | Han et al. | |
| 2012/0202871 A1* | 8/2012 | Heyes | A61K 9/0019 514/44 A |
| 2014/0248336 A1* | 9/2014 | Stein | C12N 15/1131 424/450 |
| 2014/0371432 A1 | 12/2014 | Chae et al. | |
| 2015/0274698 A1 | 10/2015 | Sandanayaka et al. | |

FOREIGN PATENT DOCUMENTS

| | | |
|---|---|---|
| KR | 10-2010-0123214 A | 11/2010 |
| KR | 10-2012-0119212 A | 10/2012 |
| KR | 101224828 B1 | 1/2013 |
| WO | 2007021142 A1 | 2/2007 |
| WO | 2010042823 A1 | 4/2010 |
| WO | 2010108108 A2 | 9/2010 |
| WO | 2011054939 A2 | 5/2011 |
| WO | 2013059496 A1 | 4/2013 |
| WO | 2013103249 A1 | 7/2013 |

OTHER PUBLICATIONS

Amarzguioui, M., et al., "Tolerance for mutations and chemical modifications in a siRNA", Nucleic Acids Research, Jan. 15, 2003, pp. 589-595, vol. 31, No. 2.

Barik, S., "Silence of the transcripts: RNA interference in medicine", J Mol Med, Jul. 19, 2005, pp. 764-773, vol. 83, No. 10.

Behlke, M., "Progress Towards in Vivo Use of siRNAs", Molecular Therapy, Feb. 14, 2006, pp. 644-670, vol. 13, No. 4.

Bertrand, J., et al., "Comparison of antisense oligonucleotides and siRNAs in cell culture and in vivo", Biochemical and Biophysical Research Communications, Aug. 30, 2002, pp. 1000-1004, vol. 296.

Braasch D., et al., "Biodistribution of phosphodiester and phosphorothioate siRNA", Bioorganic and Medicinal Chemistry Letters, Mar. 8, 2004, pp. 1139-1143, vol. 14.

Bramsen, J., et al., "A screen of chemical modifications identifies position-specific modification by UNA to most potently reduce siRNA off-target effects", Nucleic Acids Research, May 7, 2010, pp. 5761-5773, vol. 38, No. 17.

Chiu, Y., et al., "siRNA function in RNAi: A chemical modification analysis", RNA, Sep. 2003, pp. 1034-1048, vol. 9.

Crooke, S., "Progress in Antisense Technology", Annu. Rev. Med., Oct. 6, 2003, pp. 61-95, vol. 55.

Kim, S., et al., "Local and systemic delivery of VEGF siRNA using polyelectrolyte complex micelles for effective treatment of cancer", Journal of Controlled Release, Mar. 14, 2008, pp. 107-116, vol. 129.

Korrapati, A., et al., "Adenovirus Delivered Short Hairpin RNA Targeting a Conserved Site in the 5' Non-Translated Region Inhibits All Four Serotypes of Dengue Viruses", PLoS Negl. Trop. Dis., Jul. 24, 2012, pp. e1735 (1-12), vol. 6, No. 7.

Opalinska, J., et al., "Nucleic-acid therapeutics: Basic principles and recent applications", Nature Reviews: Drug Discovery, Jul. 2002, pp. 503-514, vol. 1.

Pirollo, K., et al., "Does a targeting ligand influence nanoparticle tumor localization or uptake?", Trends in Biotechnology, Aug. 21, 2008, pp. 552-558, vol. 26, No. 10.

Qui, F., et al., "Dengue in China: a clinical Review", WHO Bulletin OMS, 1993, pp. 349-359, vol. 71.

Sinha, N., et al., "Polymer support oligonucleotide synthesis XVIII: use of beta-cyanoethyl-N,N-dialkylamino-/N-morpholino phosphoramidite of deoxynucleosides for the synthesis of DNA fragments simplifying deprotection and isolation of the final product", Nucleic Acids Research, 1984, pp. 4539-4557, vol. 12, No. 11.

Sinha, R., et al., "Nanotechnology in cancer therapeutics: bioconjugated nanoparticles for drug delivery", Mol Cancer Ther, Aug. 2006, pp. 1909-1917, vol. 5, No. 8.

Soutschek, J., et al., "Therapeutic silencing of an endogenous gene by systemic administration of modified siRNAs", Nature, Nov. 11, 2004, pp. 173-178, vol. 432, No. 7014.

Tassniyom, S., et al., "Failure of High-Dose Methylprednisolone in Established Dengue Shock Syndrome: A Placebo-Controlled, Double-Blind Study", Pediatrics, Jul. 1993, pp. 111-115, vol. 92, No. 1.

Vaish, N., et al., "Improved specificity of gene silencing by siRNAs containing unlocked nucleobase analogs", Nucleic Acids Research, Nov. 2, 2010, pp. 1823-1832, vol. 39, No. 5.

Veronese, F., "Peptide and protein PEGylation: a review of problems and solutions", Biomaterials, Mar. 2001, pp. 405-417, vol. 22, No. 5.

Veronese, F., et al., "PEGylation, successful approach to drug delivery", Drug Discovery Today, Nov. 1, 2005, pp. 1451-1458, vol. 10, No. 21.

Xie, F., et al., "Harnessing in vivo siRNA delivery for drug discovery and therapeutic development", Drug Discovery Today, Jan. 2006, pp. 67-73, vol. 11, No. 1/2.

Zelphati, O., et al., "Mechanism of oligonucleotide release from cationic liposomes", Proc. Natl. Acad. Sci. USA, Oct. 15, 2006, pp. 11493-11498, vol. 93, No. 21.

Chen, P., et al., "Strand-specific 5'-O-methylation of siRNA duplexes controls guide strand selection and targeting specificity", "RNA", Dec. 19, 2007, pp. 263-274, vol. 14, No. 2.

Kim, H., et al., "Polymer-Based Hybrid Materials for Gene Delivery and Silencing", "Polymer Science and Tecnology", Jun. 2012, pp. 254-259, vol. 23, No. 3.

Kim, H., et al., "Polymer-Based Hybrid Materials for Gene Delivery and Silencing", "Polymer Science and Tecnology", Jun. 2012, pp. 254-259 (Machine Translation), vol. 23, No. 3.

Shigeta, K., et al., "Novel histidine-conjugated galactosylated cationic liposomes for efficient hepatocyte-selective gene transfer in human hepatoma HepG2 cells", "Journal of Controlled Release", Dec. 28, 2006, pp. 262-270, vol. 118.

Stein, D.A., et al., "Inhibition of Dengue Virus Infections in Cell Cultures and in AG129 Mice by a Small Interfering RNA Targeting a Highly Conserved Sequence", "Journal of Virology", Oct. 2011, pp. 10154-10166, vol. 85, No. 19.

Subramanya, S., et al., "Targeted Delivery of Small Interfering RNA to Human Dendritic Cells To Suppress Dengue Virus Infection and Associated Proinflammatory Cytokine Production", "Journal of Virology", Mar. 2010, pp. 2490-2501, vol. 84, No. 5.

Jeong, J.H., et al., "siRNA Conjugate Delivery Systems", "Bioconjugate Chem.", Jan. 2009, pp. 5-14, vol. 20, No. 1.

\* cited by examiner

FIG. 8

```
U1
H241:       TTTTAGATAGAGAGCAGATCTCTGAAAAATGAACCAACG
Universal:  TTTTAATTAGAGAGCAGATCTCTGAAAAATGAACCAACG
DENV2:      TTTTAATTAGAGAGCAGATCTCTGATGAAT--AACCAACG
Design:         AATTAGAGAGCAGATCTCT S1-1            AATTAGAGAGCAGATCTCT
S1-2             ATTAGAGAGCAGATCTCTG
S1-3              TTAGAGAGCAGATCTCTGG
S1-4               TAGAGAGCAGATCTCTGGA
S1-5                AGAGAGCAGATCTCTGGAA
S1-6                 GAGAGCAGATCTCTGGAAA
S1-7                  AGAGCAGATCTCTGGAAAA
S1-8                   GAGCAGATCTCTGGAAAAA
S1-9                    AGCAGATCTCTGGAAAAAT
S1-10                    GCAGATCTCTGGAAAAATG
S1-11                     CAGATCTCTGGAAAAATGA
S1-12                      AGATCTCTGGAAAAATGAA

DENV2:      TTTTAATTAGAGAGCAGATCTCTGATGAAT--AACCAACG

S1-13               AGAGAGCAGATCTCTGATG
S1-14                 GAGAGCAGATCTCTGATGA
S1-15                  AGAGCAGATCTCTGATGAA
S1-16                   GAGCAGATCTCTGATGAAT

U2
H241:       CTTTCAATATGCTGAAACGCGAGAGAAACCGCGT
Universal:  CTTTCAATATGCTGAAACGCGAGAGAAACCGCGT
DENV2:      CTTTCAATATGCTGAAACGCGAGAGAAACCGCGT
Design:     CTTTCAATATGCTGAAACG S2-1        CTTTCAATATGCTGAAACG
S2-2         TTTCAATATGCTGAAACGC
S2-3          TTCAATATGCTGAAACGCG
S2-4           TCAATATGCTGAAACGCGA
S2-5            CAATATGCTGAAACGCGAG
S2-6             AATATGCTGAAACGCGAGA
S2-7              ATATGCTGAAACGCGAGAG
S2-8               TATGCTGAAACGCGAGAGA
S2-9                ATGCTGAAACGCGAGAGAA
S2-10                TGCTGAAACGCGAGAGAAA
S2-11                 GCTGAAACGCGAGAGAAAC
S2-12                  CTGAAACGCGAGAGAAACC
S2-13                   TGAAACGCGAGAGAAACCG
S2-14                    GAAACGCGAGAGAAACCGC
S2-15                     AAACGCGAGAGAAACCGCG
S2-16                      AACGCGAGAGAAACCGCGT
```

FIG. 11
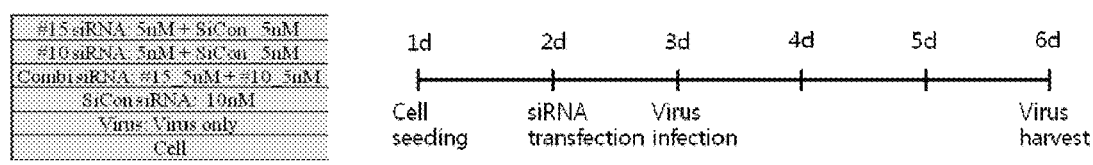
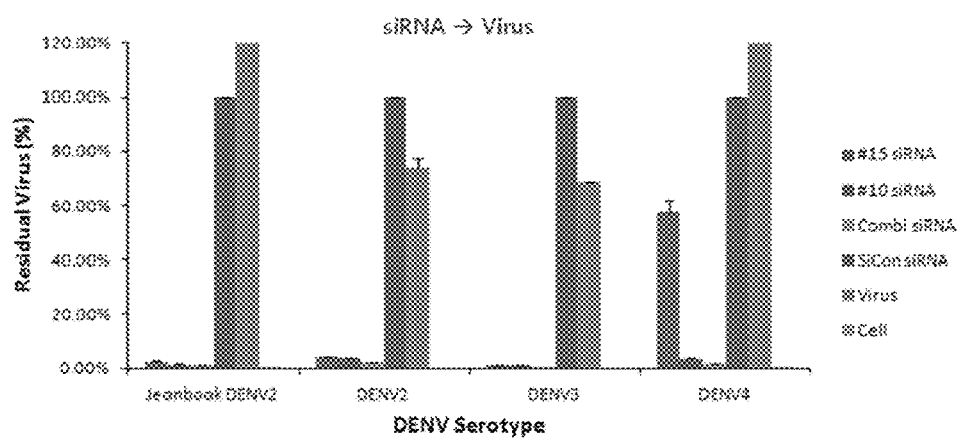

FIG. 12
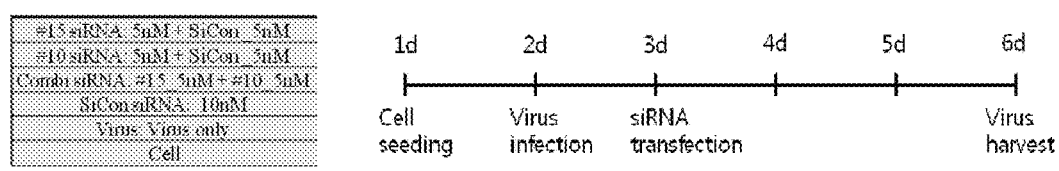
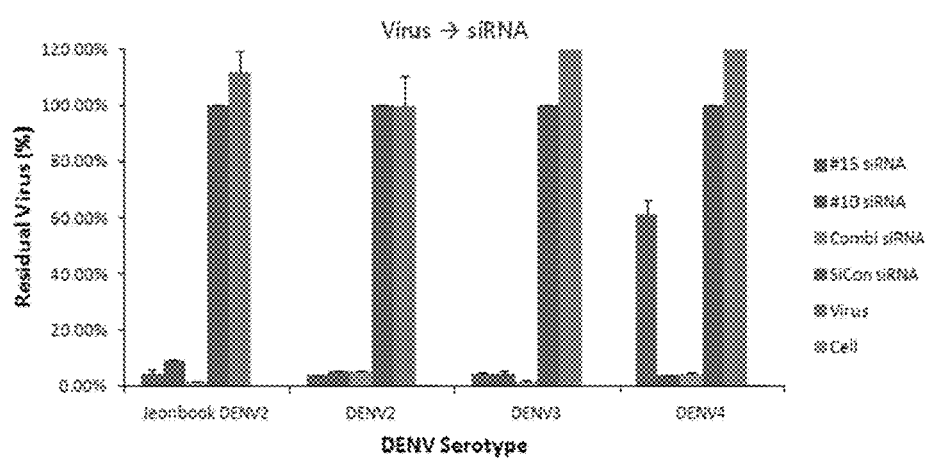

FIG. 14
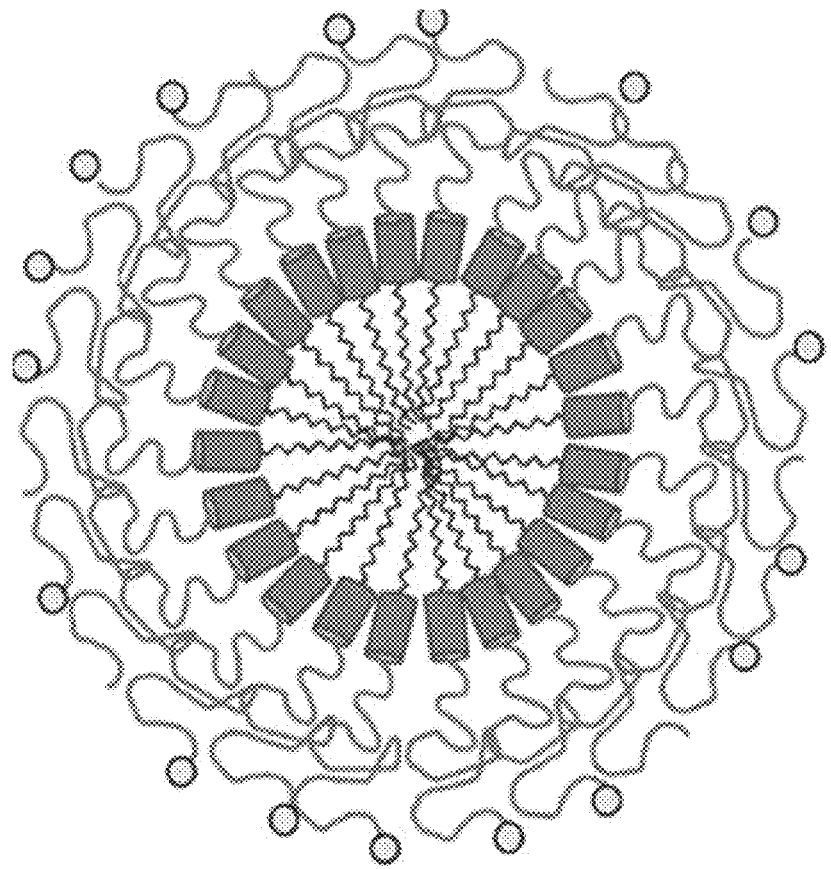
 ; Double-stranded oligo RNA Structure
~~~~~ ; Hydrophobic Material
▮ ; Double-stranded oligo RNA
~~ ; Hydrophilic Material
○ ; Target-Oriented Ligand

SEQUENCE LISTING

<160> NUMBER OF SEQ ID NOS: 89

<210> SEQ ID NO 1
<211> LENGTH: 23
<212> TYPE: DNA

```
<213> ORGANISM: Artificial Sequence
<220> FEATURE:
<223> OTHER INFORMATION: siRNA#1

<400> SEQUENCE: 1
agcagatctc tggaaaaatg aac                                              23

<210> SEQ ID NO 2
<211> LENGTH: 23
<212> TYPE: DNA
<213> ORGANISM: Artificial Sequence
<220> FEATURE:
<223> OTHER INFORMATION: siRNA#2

<400> SEQUENCE: 2
gactggattc aggaaggaga tag                                              23

<210> SEQ ID NO 3
<211> LENGTH: 21
<212> TYPE: DNA
<213> ORGANISM: Artificial Sequence
<220> FEATURE:
<223> OTHER INFORMATION: siRNA#3

<400> SEQUENCE: 3
aaggagatag gccgcatgct g                                                21

<210> SEQ ID NO 4
<211> LENGTH: 19
<212> TYPE: DNA
<213> ORGANISM: Artificial Sequence
<220> FEATURE:
<223> OTHER INFORMATION: siRNA#4

<400> SEQUENCE: 4
gcgtttcact tgtcaacaa                                                   19

<210> SEQ ID NO 5
<211> LENGTH: 19
<212> TYPE: DNA
<213> ORGANISM: Artificial Sequence
<220> FEATURE:
<223> OTHER INFORMATION: siRNA#5

<400> SEQUENCE: 5
ccagcgaaca gtcttctttt                                                  19

<210> SEQ ID NO 6
<211> LENGTH: 19
<212> TYPE: DNA
<213> ORGANISM: Artificial Sequence
<220> FEATURE:
<223> OTHER INFORMATION: siRNA#6

<400> SEQUENCE: 6
gaacagagac tttgtggaa                                                   19

<210> SEQ ID NO 7
<211> LENGTH: 23
<212> TYPE: DNA
<213> ORGANISM: Artificial Sequence
<220> FEATURE:
<223> OTHER INFORMATION: siRNA#7

<400> SEQUENCE: 7
cggagagatg tggtagacag agg                                              23
```

<210> SEQ ID NO 8
<211> LENGTH: 19
<212> TYPE: DNA
<213> ORGANISM: Artificial Sequence
<220> FEATURE:
<223> OTHER INFORMATION: siRNA#8

<400> SEQUENCE: 8
ggtccaaatt gagaacctt                                              19

<210> SEQ ID NO 9
<211> LENGTH: 19
<212> TYPE: DNA
<213> ORGANISM: Artificial Sequence
<220> FEATURE:
<223> OTHER INFORMATION: siRNA#9

<400> SEQUENCE: 9
ggaattacaa agagagaat                                              19

<210> SEQ ID NO 10
<211> LENGTH: 23
<212> TYPE: DNA
<213> ORGANISM: Artificial Sequence
<220> FEATURE:
<223> OTHER INFORMATION: siRNA#10

<400> SEQUENCE: 10
caagagacag gatgtgacag tgc                                         23

<210> SEQ ID NO 11
<211> LENGTH: 21
<212> TYPE: DNA
<213> ORGANISM: Artificial Sequence
<220> FEATURE:
<223> OTHER INFORMATION: siRNA#11

<400> SEQUENCE: 11
aagtggattc cggtgatgga a                                           21

<210> SEQ ID NO 12
<211> LENGTH: 21
<212> TYPE: DNA
<213> ORGANISM: Artificial Sequence
<220> FEATURE:
<223> OTHER INFORMATION: siRNA#12

<400> SEQUENCE: 12
aagttcgcat ggagaaattg a                                           21

<210> SEQ ID NO 13
<211> LENGTH: 23
<212> TYPE: DNA
<213> ORGANISM: Artificial Sequence
<220> FEATURE:
<223> OTHER INFORMATION: siRNA#13

<400> SEQUENCE: 13
ctcaggaaag ttctcaattg aca                                         23

<210> SEQ ID NO 14
<211> LENGTH: 19
<212> TYPE: DNA
<213> ORGANISM: Artificial Sequence
<220> FEATURE:

```
<223> OTHER INFORMATION: siRNA#14

<400> SEQUENCE: 14
agataagaga tgtgaacaa                                                    19

<210> SEQ ID NO 15
<211> LENGTH: 23
<212> TYPE: DNA
<213> ORGANISM: Artificial Sequence
<220> FEATURE:
<223> OTHER INFORMATION: siRNA#15

<400> SEQUENCE: 15
gttcaggaaa gggagttcca ttg                                               23

<210> SEQ ID NO 16
<211> LENGTH: 19
<212> TYPE: DNA
<213> ORGANISM: Artificial Sequence
<220> FEATURE:
<223> OTHER INFORMATION: siRNA#16

<400> SEQUENCE: 16
ggacagaaca gtacaaatt                                                    19

<210> SEQ ID NO 17
<211> LENGTH: 23
<212> TYPE: DNA
<213> ORGANISM: Artificial Sequence
<220> FEATURE:
<223> OTHER INFORMATION: siRNA#17

<400> SEQUENCE: 17
ccagagtctc cagcgagact agc                                               23

<210> SEQ ID NO 18
<211> LENGTH: 23
<212> TYPE: DNA
<213> ORGANISM: Artificial Sequence
<220> FEATURE:
<223> OTHER INFORMATION: siRNA#18

<400> SEQUENCE: 18
ggcatgttta cgaccaacat atg                                               23

<210> SEQ ID NO 19
<211> LENGTH: 21
<212> TYPE: DNA
<213> ORGANISM: Artificial Sequence
<220> FEATURE:
<223> OTHER INFORMATION: siRNA#19

<400> SEQUENCE: 19
aagcatctct cattgaagtg a                                                 21

<210> SEQ ID NO 20
<211> LENGTH: 19
<212> TYPE: DNA
<213> ORGANISM: Artificial Sequence
<220> FEATURE:
<223> OTHER INFORMATION: siRNA#20

<400> SEQUENCE: 20
ccatggcact tgggcaaat                                                    19
```

```
<210> SEQ ID NO 21
<211> LENGTH: 19
<212> TYPE: DNA
<213> ORGANISM: Artificial Sequence
<220> FEATURE:
<223> OTHER INFORMATION: siRNA#21

<400> SEQUENCE: 21
ggagatagac tttggagaa                                                   19

<210> SEQ ID NO 22
<211> LENGTH: 19
<212> TYPE: DNA
<213> ORGANISM: Artificial Sequence
<220> FEATURE:
<223> OTHER INFORMATION: siRNA#22

<400> SEQUENCE: 22
ggatggaaat taggccctt                                                   19

<210> SEQ ID NO 23
<211> LENGTH: 19
<212> TYPE: DNA
<213> ORGANISM: Artificial Sequence
<220> FEATURE:
<223> OTHER INFORMATION: siRNA#23

<400> SEQUENCE: 23
gaagaatgct tgaggagaa                                                   19

<210> SEQ ID NO 24
<211> LENGTH: 23
<212> TYPE: DNA
<213> ORGANISM: Artificial Sequence
<220> FEATURE:
<223> OTHER INFORMATION: siRNA#24

<400> SEQUENCE: 24
accataatgg ctgtgttgtt tgt                                              23

<210> SEQ ID NO 25
<211> LENGTH: 23
<212> TYPE: DNA
<213> ORGANISM: Artificial Sequence
<220> FEATURE:
<223> OTHER INFORMATION: siRNA#25

<400> SEQUENCE: 25
gccagtgtac ctaatgactc tca                                              23

<210> SEQ ID NO 26
<211> LENGTH: 19
<212> TYPE: DNA
<213> ORGANISM: Artificial Sequence
<220> FEATURE:
<223> OTHER INFORMATION: siRNA#26

<400> SEQUENCE: 26
gaaaggagct tcaaagaga                                                   19

<210> SEQ ID NO 27
<211> LENGTH: 19
<212> TYPE: DNA
<213> ORGANISM: Artificial Sequence
<220> FEATURE:
<223> OTHER INFORMATION: siRNA#27
```

<400> SEQUENCE: 27
gtataatggc tgtgggttt    19

<210> SEQ ID NO 28
<211> LENGTH: 21
<212> TYPE: DNA
<213> ORGANISM: Artificial Sequence
<220> FEATURE:
<223> OTHER INFORMATION: siRNA#28

<400> SEQUENCE: 28
aagatgttca ggttctagct a    21

<210> SEQ ID NO 29
<211> LENGTH: 23
<212> TYPE: DNA
<213> ORGANISM: Artificial Sequence
<220> FEATURE:
<223> OTHER INFORMATION: siRNA#29

<400> SEQUENCE: 29
gaacatctgg ttctcccatc att    23

<210> SEQ ID NO 30
<211> LENGTH: 23
<212> TYPE: DNA
<213> ORGANISM: Artificial Sequence
<220> FEATURE:
<223> OTHER INFORMATION: siRNA#30

<400> SEQUENCE: 30
cggactctac ggaaatggag tag    23

<210> SEQ ID NO 31
<211> LENGTH: 19
<212> TYPE: DNA
<213> ORGANISM: Artificial Sequence
<220> FEATURE:
<223> OTHER INFORMATION: siRNA#31

<400> SEQUENCE: 31
tagaagacat cgagagaga    19

<210> SEQ ID NO 32
<211> LENGTH: 19
<212> TYPE: DNA
<213> ORGANISM: Artificial Sequence
<220> FEATURE:
<223> OTHER INFORMATION: siRNA#32

<400> SEQUENCE: 32
ccagaaaggt catggaaca    19

<210> SEQ ID NO 33
<211> LENGTH: 23
<212> TYPE: DNA
<213> ORGANISM: Artificial Sequence
<220> FEATURE:
<223> OTHER INFORMATION: siRNA#33

<400> SEQUENCE: 33
gactggataa ccgactacca agg    23

<210> SEQ ID NO 34
<211> LENGTH: 23

<212> TYPE: DNA
<213> ORGANISM: Artificial Sequence
<220> FEATURE:
<223> OTHER INFORMATION: siRNA#34

<400> SEQUENCE: 34
aagaaaacat ggaggttgaa att                                        23

<210> SEQ ID NO 35
<211> LENGTH: 19
<212> TYPE: DNA
<213> ORGANISM: Artificial Sequence
<220> FEATURE:
<223> OTHER INFORMATION: siRNA#35

<400> SEQUENCE: 35
aggaaaagga atagggaaa                                             19

<210> SEQ ID NO 36
<211> LENGTH: 21
<212> TYPE: DNA
<213> ORGANISM: Artificial Sequence
<220> FEATURE:
<223> OTHER INFORMATION: siRNA#36

<400> SEQUENCE: 36
aagacaatca attgatctac g                                          21

<210> SEQ ID NO 37
<211> LENGTH: 23
<212> TYPE: DNA
<213> ORGANISM: Artificial Sequence
<220> FEATURE:
<223> OTHER INFORMATION: siRNA#37

<400> SEQUENCE: 37
aacgaccttg atagcatcct tag                                        23

<210> SEQ ID NO 38
<211> LENGTH: 19
<212> TYPE: DNA
<213> ORGANISM: Artificial Sequence
<220> FEATURE:
<223> OTHER INFORMATION: siRNA#38

<400> SEQUENCE: 38
agtaatagat ctagaacca                                             19

<210> SEQ ID NO 39
<211> LENGTH: 23
<212> TYPE: DNA
<213> ORGANISM: Artificial Sequence
<220> FEATURE:
<223> OTHER INFORMATION: siRNA#39

<400> SEQUENCE: 39
aagagacagc taaactcact aga                                        23

<210> SEQ ID NO 40
<211> LENGTH: 19
<212> TYPE: DNA
<213> ORGANISM: Artificial Sequence
<220> FEATURE:
<223> OTHER INFORMATION: siRNA#40

<400> SEQUENCE: 40

-continued gtacaaaaga agtggaata                                              19

<210> SEQ ID NO 41
<211> LENGTH: 19
<212> TYPE: DNA
<213> ORGANISM: Artificial Sequence
<220> FEATURE:
<223> OTHER INFORMATION: siRNA#41

<400> SEQUENCE: 41
ggtaaaacca aagggaaa                                               19

<210> SEQ ID NO 42
<211> LENGTH: 19
<212> TYPE: DNA
<213> ORGANISM: Artificial Sequence
<220> FEATURE:
<223> OTHER INFORMATION: siRNA#42

<400> SEQUENCE: 42
ggaagaacat taagagttt                                              19

<210> SEQ ID NO 43
<211> LENGTH: 19
<212> TYPE: DNA
<213> ORGANISM: Artificial Sequence
<220> FEATURE:
<223> OTHER INFORMATION: siRNA#43

<400> SEQUENCE: 43
tggagaaact gcagagaaa                                              19

<210> SEQ ID NO 44
<211> LENGTH: 23
<212> TYPE: DNA
<213> ORGANISM: Artificial Sequence
<220> FEATURE:
<223> OTHER INFORMATION: siRNA#44

<400> SEQUENCE: 44
atcaggaaaa cccatacaga acc                                         23

<210> SEQ ID NO 45
<211> LENGTH: 19
<212> TYPE: DNA
<213> ORGANISM: Artificial Sequence
<220> FEATURE:
<223> OTHER INFORMATION: siRNA#45

<400> SEQUENCE: 45 ccaaagggt tgaaagaaa                                               19

<210> SEQ ID NO 46
<211> LENGTH: 19
<212> TYPE: DNA
<213> ORGANISM: Artificial Sequence
<220> FEATURE:
<223> OTHER INFORMATION: siRNA#46

<400> SEQUENCE: 46
ggatggagtt taagagaaa                                              19

<210> SEQ ID NO 47
<211> LENGTH: 23
<212> TYPE: DNA
<213> ORGANISM: Artificial Sequence

```
<220> FEATURE:
<223> OTHER INFORMATION: siRNA#47

<400> SEQUENCE: 47
tccagttcat tcgtgggaag aca                                    23

<210> SEQ ID NO 48
<211> LENGTH: 23
<212> TYPE: DNA
<213> ORGANISM: Artificial Sequence
<220> FEATURE:
<223> OTHER INFORMATION: siRNA#48

<400> SEQUENCE: 48
ggcatattgg actagcggtt aga                                    23

<210> SEQ ID NO 49
<211> LENGTH: 19
<212> TYPE: DNA
<213> ORGANISM: Artificial Sequence
<220> FEATURE:
<223> OTHER INFORMATION: siRNA#49

<400> SEQUENCE: 49
gcatattgac gctgggaaa                                         19

<210> SEQ ID NO 50
<211> LENGTH: 23
<212> TYPE: DNA
<213> ORGANISM: Artificial Sequence
<220> FEATURE:
<223> OTHER INFORMATION: siRNA#50

<400> SEQUENCE: 50
accagagatc ctgctgtctc tgc                                    23

<210> SEQ ID NO 51
<211> LENGTH: 21
<212> TYPE: DNA
<213> ORGANISM: Artificial Sequence
<220> FEATURE:
<223> OTHER INFORMATION: siRNA#51

<400> SEQUENCE: 51
agagagcaga ucucuggaaa a                                      21

<210> SEQ ID NO 52
<211> LENGTH: 21
<212> TYPE: DNA
<213> ORGANISM: Artificial Sequence
<220> FEATURE:
<223> OTHER INFORMATION: siRNA#52

<400> SEQUENCE: 52
ucaauaugcu gaaacgcgag a                                      21

<210> SEQ ID NO 53
<211> LENGTH: 21
<212> TYPE: DNA
<213> ORGANISM: Artificial Sequence
<220> FEATURE:
<223> OTHER INFORMATION: siRNA#53

<400> SEQUENCE: 53
gguuagagga gaccccuccc a                                      21
```

```
<210> SEQ ID NO 54
<211> LENGTH: 21
<212> TYPE: DNA
<213> ORGANISM: Artificial Sequence
<220> FEATURE:
<223> OTHER INFORMATION: siRNA#54

<400> SEQUENCE: 54
ggacuagagg uuagaggaga c                                              21

<210> SEQ ID NO 55
<211> LENGTH: 21
<212> TYPE: DNA
<213> ORGANISM: Artificial Sequence
<220> FEATURE:
<223> OTHER INFORMATION: siRNA#55

<400> SEQUENCE: 55
aaacagcaua uugacgcugg g                                              21

<210> SEQ ID NO 56
<211> LENGTH: 21
<212> TYPE: DNA
<213> ORGANISM: Artificial Sequence
<220> FEATURE:
<223> OTHER INFORMATION: siRNA#56

<400> SEQUENCE: 56
gaccagagau ccugcugucu c                                              21

<210> SEQ ID NO 57
<211> LENGTH: 19
<212> TYPE: DNA
<213> ORGANISM: Artificial Sequence
<220> FEATURE:
<223> OTHER INFORMATION: SiRNA#51-1

<400> SEQUENCE: 57
aauuagagag cagaucucu                                                 19

<210> SEQ ID NO 58
<211> LENGTH: 19
<212> TYPE: DNA
<213> ORGANISM: Artificial Sequence
<220> FEATURE:
<223> OTHER INFORMATION: SiRNA#51-2

<400> SEQUENCE: 58
auuagagagc agaucucug                                                 19

<210> SEQ ID NO 59
<211> LENGTH: 19
<212> TYPE: DNA
<213> ORGANISM: Artificial Sequence
<220> FEATURE:
<223> OTHER INFORMATION: SiRNA#51-3

<400> SEQUENCE: 59
uuagagagca gaucucugg                                                 19

<210> SEQ ID NO 60
<211> LENGTH: 19
<212> TYPE: DNA
<213> ORGANISM: Artificial Sequence
<220> FEATURE:
<223> OTHER INFORMATION: SiRNA#51-4
```

```
<400> SEQUENCE: 60
uagagagcag aucucugga                                                    19

<210> SEQ ID NO 61
<211> LENGTH: 19
<212> TYPE: DNA
<213> ORGANISM: Artificial Sequence
<220> FEATURE:
<223> OTHER INFORMATION: SiRNA#51-5

<400> SEQUENCE: 61
agagagcaga ucucuggaa                                                    19

<210> SEQ ID NO 62
<211> LENGTH: 19
<212> TYPE: DNA
<213> ORGANISM: Artificial Sequence
<220> FEATURE:
<223> OTHER INFORMATION: SiRNA#51-6

<400> SEQUENCE: 62
gagagcagau cucuggaaa                                                    19

<210> SEQ ID NO 63
<211> LENGTH: 19
<212> TYPE: DNA
<213> ORGANISM: Artificial Sequence
<220> FEATURE:
<223> OTHER INFORMATION: SiRNA#51-7

<400> SEQUENCE: 63
agagcagauc ucuggaaaa                                                    19

<210> SEQ ID NO 64
<211> LENGTH: 19
<212> TYPE: DNA
<213> ORGANISM: Artificial Sequence
<220> FEATURE:
<223> OTHER INFORMATION: SiRNA#51-8

<400> SEQUENCE: 64
gagcagaucu cuggaaaaa                                                    19

<210> SEQ ID NO 65
<211> LENGTH: 19
<212> TYPE: DNA
<213> ORGANISM: Artificial Sequence
<220> FEATURE:
<223> OTHER INFORMATION: SiRNA#51-9

<400> SEQUENCE: 65
agcagaucuc uggaaaaau                                                    19

<210> SEQ ID NO 66
<211> LENGTH: 19
<212> TYPE: DNA
<213> ORGANISM: Artificial Sequence
<220> FEATURE:
<223> OTHER INFORMATION: SiRNA#51-10

<400> SEQUENCE: 66
gcagaucucu ggaaaaaug                                                    19

<210> SEQ ID NO 67
```

<210> SEQ ID NO 67
<211> LENGTH: 19
<212> TYPE: DNA
<213> ORGANISM: Artificial Sequence
<220> FEATURE:
<223> OTHER INFORMATION: SiRNA#51-11

<400> SEQUENCE: 67
cagaucucug gaaaauga                                                  19

<210> SEQ ID NO 68
<211> LENGTH: 19
<212> TYPE: DNA
<213> ORGANISM: Artificial Sequence
<220> FEATURE:
<223> OTHER INFORMATION: SiRNA#51-12

<400> SEQUENCE: 68
agaucucugg aaaaugaa                                                  19

<210> SEQ ID NO 69
<211> LENGTH: 19
<212> TYPE: DNA
<213> ORGANISM: Artificial Sequence
<220> FEATURE:
<223> OTHER INFORMATION: SiRNA#51-13

<400> SEQUENCE: 69
agagagcaga ucucugaug                                                 19

<210> SEQ ID NO 70
<211> LENGTH: 19
<212> TYPE: DNA
<213> ORGANISM: Artificial Sequence
<220> FEATURE:
<223> OTHER INFORMATION: SiRNA#51-14

<400> SEQUENCE: 70
gagagcagau cucugauga                                                 19

<210> SEQ ID NO 71
<211> LENGTH: 19
<212> TYPE: DNA
<213> ORGANISM: Artificial Sequence
<220> FEATURE:
<223> OTHER INFORMATION: SiRNA#51-15

<400> SEQUENCE: 71
agagcagauc ucugaugaa                                                 19

<210> SEQ ID NO 72
<211> LENGTH: 19
<212> TYPE: DNA
<213> ORGANISM: Artificial Sequence
<220> FEATURE:
<223> OTHER INFORMATION: SiRNA#51-16

<400> SEQUENCE: 72
gagcagaucu cugaugaau                                                 19

<210> SEQ ID NO 73
<211> LENGTH: 19
<212> TYPE: DNA
<213> ORGANISM: Artificial Sequence
<220> FEATURE:
<223> OTHER INFORMATION: SiRNA#52-1

<400> SEQUENCE: 73
cuuucaauau gcugaaacg                                                19

<210> SEQ ID NO 74
<211> LENGTH: 19
<212> TYPE: DNA
<213> ORGANISM: Artificial Sequence
<220> FEATURE:
<223> OTHER INFORMATION: SiRNA#52-2

<400> SEQUENCE: 74
uuucaauaug cugaaacgc                                                19

<210> SEQ ID NO 75
<211> LENGTH: 19
<212> TYPE: DNA
<213> ORGANISM: Artificial Sequence
<220> FEATURE:
<223> OTHER INFORMATION: SiRNA#52-3

<400> SEQUENCE: 75
uucaauaugc ugaaacgcg                                                19

<210> SEQ ID NO 76
<211> LENGTH: 19
<212> TYPE: DNA
<213> ORGANISM: Artificial Sequence
<220> FEATURE:
<223> OTHER INFORMATION: SiRNA#52-4

<400> SEQUENCE: 76
ucaauaugcu gaaacgcga                                                19

<210> SEQ ID NO 77
<211> LENGTH: 19
<212> TYPE: DNA
<213> ORGANISM: Artificial Sequence
<220> FEATURE:
<223> OTHER INFORMATION: SiRNA#52-5

<400> SEQUENCE: 77
caauaugcug aaacgcgag                                                19

<210> SEQ ID NO 78
<211> LENGTH: 19
<212> TYPE: DNA
<213> ORGANISM: Artificial Sequence
<220> FEATURE:
<223> OTHER INFORMATION: SiRNA#52-6

<400> SEQUENCE: 78
aauaugcuga aacgcgaga                                                19

<210> SEQ ID NO 79
<211> LENGTH: 19
<212> TYPE: DNA
<213> ORGANISM: Artificial Sequence
<220> FEATURE:
<223> OTHER INFORMATION: SiRNA#52-7

<400> SEQUENCE: 79
auaugcugaa acgcgagag                                                19

<210> SEQ ID NO 80
<211> LENGTH: 19
<212> TYPE: DNA

```
<213> ORGANISM: Artificial Sequence
<220> FEATURE:
<223> OTHER INFORMATION: SiRNA#52-8

<400> SEQUENCE: 80
uaugcugaaa cgcgagaga                                            19

<210> SEQ ID NO 81
<211> LENGTH: 19
<212> TYPE: DNA
<213> ORGANISM: Artificial Sequence
<220> FEATURE:
<223> OTHER INFORMATION: SiRNA#52-9

<400> SEQUENCE: 81
augcugaaac gcgagagaa                                            19

<210> SEQ ID NO 82
<211> LENGTH: 19
<212> TYPE: DNA
<213> ORGANISM: Artificial Sequence
<220> FEATURE:
<223> OTHER INFORMATION: SiRNA#52-10

<400> SEQUENCE: 82
ugcugaaacg cgagagaaa                                            19

<210> SEQ ID NO 83
<211> LENGTH: 19
<212> TYPE: DNA
<213> ORGANISM: Artificial Sequence
<220> FEATURE:
<223> OTHER INFORMATION: SiRNA#52-11

<400> SEQUENCE: 83
gcugaaacgc gagagaaac                                            19

<210> SEQ ID NO 84
<211> LENGTH: 19
<212> TYPE: DNA
<213> ORGANISM: Artificial Sequence
<220> FEATURE:
<223> OTHER INFORMATION: SiRNA#52-12

<400> SEQUENCE: 84
cugaaacgcg agagaaacc                                            19

<210> SEQ ID NO 85
<211> LENGTH: 19
<212> TYPE: DNA
<213> ORGANISM: Artificial Sequence
<220> FEATURE:
<223> OTHER INFORMATION: SiRNA#52-13

<400> SEQUENCE: 85
ugaaacgcga gagaaaccg                                            19

<210> SEQ ID NO 86
<211> LENGTH: 19
<212> TYPE: DNA
<213> ORGANISM: Artificial Sequence
<220> FEATURE:
<223> OTHER INFORMATION: SiRNA#52-14

<400> SEQUENCE: 86
gaaacgcgag agaaaccgc                                            19
```

```
<210> SEQ ID NO 87
<211> LENGTH: 19
<212> TYPE: DNA
<213> ORGANISM: Artificial Sequence
<220> FEATURE:
<223> OTHER INFORMATION: SiRNA#52-15

<400> SEQUENCE: 87
aaacgcgaga gaaaccgcg                                                    19

<210> SEQ ID NO 88
<211> LENGTH: 19
<212> TYPE: DNA
<213> ORGANISM: Artificial Sequence
<220> FEATURE:
<223> OTHER INFORMATION: SiRNA#52-16

<400> SEQUENCE: 88
aacgcgagag aaaccgcgu                                                    19

<210> SEQ ID NO 89
<211> LENGTH: 19
<212> TYPE: DNA
<213> ORGANISM: Artificial Sequence
<220> FEATURE:
<223> OTHER INFORMATION: siCONT

<400> SEQUENCE: 89
cuuacgcuga guacuucga                                                    19
```

DENGUE VIRUS-SPECIFIC SIRNA, DOUBLE HELIX OLIGO-RNA STRUCTURE COMPRISING SIRNA, AND COMPOSITION FOR SUPPRESSING PROLIFERATION OF DENGUE VIRUS COMPRISING RNA STRUCTURE

TECHNICAL FIELD

The present invention relates to a dengue virus-specific siRNA, a double-stranded oligo RNA structure comprising the siRNA, and a composition for inhibiting dengue virus replication, which comprises the same, in which the double-stranded oligo RNA structure comprises a hydrophilic compound and hydrophobic compound conjugated to both ends of the double-stranded RNA (siRNA) by a single covalent bond or a linker-mediated covalent bond so as to be efficiently delivered into cells, and can be converted into nanoparticles by hydrophobic interactions between the double-stranded oligo RNA structures in an aqueous solution. The siRNA included in the double-stranded oligo RNA structures is preferably a dengue virus-specific siRNA.

Moreover, the present invention relates to a method for preparing the double-stranded oligo RNA structure, and a pharmaceutical composition for the inhibition of dengue virus replication and the prevention and treatment of dengue viral infection, which comprises the double-stranded oligo RNA structure.

BACKGROUND ART

Dengue virus is a virus belonging to the family Flaviviridae, which has a single strand RNA and a single envelope having a diameter of 30 nm and shows positive polarity. It is one of disease that most commonly affect people in the world. Dengue fever is transmitted by mosquito bites or infected people, causes a high fever and rash with muscle and joint pains, and also causes hemorrhage in some cases. People with dengue hemorrhagic fever are high risk of losing their life. In addition, people have permanent immunity against a dengue viral type that infected them, but are not protected from other viral types. For this reason, in the case people who live in endemic area, infections with all four types of dengue virus may occur throughout their life.

The World Health Organization estimates that over 50 million dengue infected people and over one million dengue infected patients each year in worldwide occur. Thus, dengue is considered as one of key public health issues, but a dengue virus preventive vaccine has not yet been reported. Southeastern Asia is the largest endemic area for dengue fever, in which reinfections with several serotypes of dengue virus easily occur. Dengue hemorrhagic fever (DHF) and dengue shock syndrome (DSS) in secondary dengue infections are the major causes of death (Qiu F X et al., *Bull World Health Organ,* 71:349-359, 1993; Tassniyom S et al., *Pediatrics,* 92:111-115, 1993). In Korea, an outbreak of dengue fever has not yet occurred, but it is expected that the number of Korean people infected with dengue virus will increase due to the expansion of trade with dengue endemic areas, trip abroad, overseas residence and the like. In addition, an increase in infection opportunities such as off-road traveling and repeated visits to dengue endemic areas can increase the possibility of reinfection with dengue virus and can also increase the risk of development of DHF or DSS by secondary infection. In fact, in the Korea National Institute of Health, serological tests for 99 persons, who returned from abroad and showed symptoms suspected as dengue fever, were performed during a period from 2001 to June, 2003, and 33 people positive for dengue virus antibodies were found.

Dengue virus has four serotypes and a genome size of about 11 kb. The dengue virus genome is translated into a single polyprotein, and then cleaved into functional proteins by host or viral proteases into functional proteins. In a previous vaccine strategy, there was great difficulty in inhibiting dengue virus replication, because effective protection against four similar serotypes with a polyvalent vaccine was not induced. However, in a genetic engineering approach for the viral genome, studies on a vaccine effective against all the four serotypes are in progress, and final clinical trials are in progress by a certain multi-national pharmaceutical company. Generally, primary infection is not fatal, but when secondary infection with different serotypes occurs, effective protection will not be made due to a previously formed antibody, and the viral infection will be increased by ADCC (antibody dependent cell cytotoxicity) to pose great threat to life. To date, only a primary approach has been performed in which cytokine is administered to such patients. Meanwhile, technologies of inhibiting the expression of genes are an important tool in developing a therapeutic agent for treating diseases and validating a target. Since the roles of RNA interference (hereinafter referred to as 'RNAi') among these technologies was found, it was found that the RNAi acts on sequence-specific mRNA in various kinds of mammalian cells (Silence of the Transcripts: RNA Interference in Medicine. J Mol Med (2005) 83: 764-773). When long-chain double-stranded RNA is delivered into cells, the delivered double stranded RNA is converted into a small interfering RNA (hereinafter referred to as 'siRNA') processed into 21 to 23 base pairs (bp) by the endonuclease Dicer, wherein the siRNA inhibits the expression of the target gene in a sequence-specific manner by a process in which the antisense strand recognizes and degrades the target mRNA (NUCLEIC-ACID THERAPEUTICS: BASIC PRINCIPLES AND RECENT APPLICATIONS. Nature Reviews Drug Discovery. 2002. 1, 503-514).

Bertrand et al. have reported that siRNA has an excellent inhibitory effect on the expression of mRNA in vitro and in vivo compared to an antisense oligonucleotide (ASO) for the same target gene and that the effect is long lasting (Comparison of antisense oligonucleotides and siRNAs in cell culture and in vivo. Biochem. Biophys. Res. Commun. 2002. 296: 1000-1004). Also, because siRNA complementarily binds to the target mRNA to regulate the expression of the target gene in a sequence-specific manner, it can be advantageously used in a wider range of applications compared to conventional antibody-based drugs or chemicals (small molecule drugs) (Progress Towards in Vivo Use of siRNAs. MOLECMLAR THERAPY. 2006 13(4):664-670).

siRNA has excellent effects and can be used in a wide range of applications, but in order for siRNA to be developed into therapeutic agents, it is required to improve the in vivo stability and intracellular delivery efficiency of siRNA so as to effectively deliver siRNA into its target cells (Harnessing in vivo siRNA delivery for drug discovery and therapeutic development. Drug Discov Today. 2006 January; 11(1-2):67-73).

In order to solve the above-mentioned problem, studies on a technology of either modifying some nucleotides of siRNA or the backbone of siRNA to improve the in vivo stability so as to have resistance against nuclease or using carriers such as a viral vector, liposome or nanoparticles have been actively conducted.

Delivery systems comprising a viral vector such as adenovirus or retrovirus have high transfection efficiency, carry the risks of immunogenicity and oncogenicity. However, non-viral carriers including nanoparticles are evaluated to have low intracellular delivery efficiency compared to viral carriers, but have advantages, including high safety in vivo, target-specific delivery, efficient uptake and internalization of RNAi oligonucleotides into cells or tissues, and low cytotoxicity and immune stimulation. Thus, these non-viral carriers are considered as a promising delivery method compared to the vial delivery system (Nonviral delivery of synthetic siRNA s in vivo. J Clin Invest. 2007 December 3; 117(12): 3623-3632).

In a method of using nanocarriers among the non-viral delivery systems, nanoparticles are formed using various polymers such as liposome, a cationic polymer complex and the like, and iRNA is supported on these nanoparticles that are nanocarriers, and is delivered into the cell. In the method of using nanocarriers, a polymeric nanoparticle, polymer micelle, lipoplex and the like are mainly used. Among them, the lipoplex is composed of cationic lipid and interacts with anionic lipid of endosome in the cell to destabilize the endosome, thereby serving to deliver the iRNA into the cell (Proc. Natl. Acad. Sci. 15; 93(21):11493-8, 1996).

In addition, it is known that the efficiency of siRNA in vivo can be increased by conjugating a chemical compound or the like to the end region of the passenger (sense) strand of the siRNA so as to have improved pharmacokinetic characteristics (Nature 11; 432(7014):173-8, 2004). In this case, the stability of the siRNA changes depending on the property of the chemical compound conjugated to the end of the sense (passenger) or antisense (guide) strand of the siRNA. For example, siRNA conjugated with a polymer compound such as polyethylene glycol (PEG) interacts with the anionic phosphoric acid group of siRNA in the presence of a cationic compound to form a complex, thereby providing a carrier having improved siRNA stability (J Control Release 129(2):107-16, 2008). Particularly, micelles made of a polymer complex have a very small size and a very uniform size distribution compared to other drug delivery systems such as microspheres or nanoparticles, and are spontaneously formed. Thus, these micelles have advantages in that the quality of the formulation is easily managed and the reproducibility thereof is easily secured.

Further, in order to improve the intracellular delivery efficiency of siRNA, a technology for securing the stability of the siRNA and increasing the cell membrane permeability of the siRNA using a siRNA conjugate obtained by conjugating a hydrophilic compound (for example, polyethylene glycol (PEG)), which is a biocompatible polymer, to the siRNA via a simple covalent bond or a linker-mediated covalent bond, has been developed (Korean Patent Registration No. 883471). However, even when the siRNA is chemically modified and conjugated to polyethylene glycol (PEG) (PEGylation), it still has low stability in vivo and a disadvantage in that it is not easily delivered into a target organ. In order to solve these disadvantages, double-stranded oligo RNA structures comprising hydrophilic and hydrophobic compounds bound to an oligonucleotide, particularly double-stranded oligo RNA such as siRNA have been developed. These structures form self-assembled nanoparticles, named SAMiRNA™ (Self Assembled Micelle Inhibitory RNA), by hydrophobic interaction of the hydrophobic compound (see Korean Patent Registration No. 1224828). The SAMiRNA™ technology has advantages over conventional delivery technologies in that homogenous nanoparticles having a very small size can be obtained.

Specifically, in the SAMiRNA™ technology, PEG (polyethylene glycol) is used as the hydrophilic compound. PEG is a synthetic polymer and is generally used to increase the solubility of medical drugs, particularly proteins, and control the pharmacokinetics of drugs. PEG is a polydisperse material, and a one-batch polymer is made up of different numbers of monomers, and thus shows a molecular weight in the form of a gauss curve. Also, the homogeneity of a material is expressed as the polydisperse index (Mw/Mn). In other words, when PEG has a low molecular weight (3-5 kDa), it shows a polydisperse index of about 1.01, and when it has a high molecular weight (20 kDa), it shows a high a polydisperse index of about 1.2, indicating that the homogeneity of PEG decreases as the molecular weight of PEG increases (F. M. Veronese. Peptide and protein PEGylation: a review of problems and solutions. Biomaterials (2001) 22:405-417). Thus, when PEG is bound to a medical drug, there is a disadvantage in that the polydisperse properties of PEG are reflected to the conjugate so that the verification of a single material is not easy. Due to this disadvantage, processes for the synthesis and purification of PEG have been improved in order to produce materials having a low polydisperse index. However, when PEG is bound to a compound having a low molecular weight, there are problems associated with the polydisperse properties of the compound, causing a problem in that it is not easy to confirm whether the binding was easily achieved (Francesco M. Veronese and Gianfranco Pasut. PEGylation, successful approach to drug delivery. DRUG DISCOVERY TODAY (2005) 10(21):1451-1458).

Accordingly, in recent years, the SAMiRNA™ technology (that is self-assembled nanoparticles) has been improved by forming the hydrophilic compound of the double-stranded RNA structure (constituting SAMiRNA™) into basic unit blocks, each comprising 1-15 monomers having a uniform molecular weight, and if necessary, a linker, so that a suitable number of the blocks will be used, if required. Thus, new types of delivery system technologies, which have small sizes and significantly improved polydisperse properties, compared to conventional SAMiRNA™, have been developed.

As described above, a therapeutic agent having an excellent therapeutic effect against most serotypes of dengue virus is not currently present, and conventional vaccination methods have limitations. Thus, there is an urgent need for the treatment of a new type of therapeutic agent. A dengue virus infection therapeutic agent based on RNAi technology has a potential to be used as an alternative thereto, but an effective therapeutic agent based on RNAi technology, particularly a therapeutic agent having a therapeutic effect against all dengue virus serotypes, has not yet been developed.

DISCLOSURE OF INVENTION

Technical Problem

The present inventors have made extensive efforts to solve the above-described problems, and as a result, have found that a siRNA candidate derived from the conserved sequence of dengue virus inhibits the replication of all dengue virus serotypes with high efficiency, thereby completing the present invention.

Therefore, it is an object of the present invention to provide a novel siRNA capable of inhibiting the expression of serotypes 1, 2, 3 and 4 of dengue virus with very high efficiency in a manner specific for the serotypes, a double-stranded oligo RNA structure comprising the novel siRNA, and a method for preparing the double-stranded oligo RNA structure.

Another object of the present invention is to provide a pharmaceutical composition for the inhibition of dengue virus replication and/or the prevention and treatment of dengue virus infection, which contains, as an active ingredient, the dengue virus-specific siRNA or the double-stranded oligo RNA structure comprising the siRNA.

Still another object of the present invention is to provide a method for the inhibition of dengue virus replication and/or the prevention and treatment of dengue virus infection, which comprises using the dengue virus-specific siRNA or the double-stranded oligo RNA structure comprising the siRNA.

Technical Solution

The present invention provides a dengue virus-specific siRNA comprising a first oligonucleotide which is a sense strand having any one sequence selected from among SEQ ID NO: 1 to SEQ ID NO: 88, and a second oligonucleotide which is an antisense strand having a sequence complementary to that of the sense strand.

As used herein, the term "siRNA" is intended to include all materials having general RNAi (RNA interference) activity, and it will be obvious to those skilled in the art that the dengue virus-specific siRNA also includes dengue virus-specific shRNA and the like.

Each of the sequences of SEQ ID NO: 1 to SEQ ID NO: 88 is the sense strand sequence of the dengue virus-specific siRNA, and targets a conserved region present in all dengue virus serotypes. Thus, it has the property of inhibiting the replication of all dengue virus serotypes, thereby exhibiting the effect of preventing and/or treating dengue virus infection.

The siRNA according to the present invention preferably comprises a dengue virus-specific siRNA sense strand having a sequence set forth in any one of SEQ ID NOS: 4 to 8, 13, 16, 20, 22, 23, 29, 32, 34, 39 to 42, 44 to 47, 51, 52, 70 to 72, 76, 77 and 80 to 82. More preferably, it comprises a dengue virus-specific siRNA sense strand having a sequence set forth in any one of SEQ ID NOS: 4, 16, 22, 51, 52, 71 and 82. Most preferably, it comprises a dengue virus-specific siRNA sense strand having a sequence set forth in any one of SEQ ID NOS: 51, 52, 71 and 82.

The sense strand or antisense strand of the siRNA according to the present invention preferably consists of 19 to 31 nucleotides, and the siRNA according to the present invention comprises a sense strand having a sequence of any one selected from the sequences of SEQ ID NO: 1 to SEQ ID NO: 88, and an antisense strand complementary thereto.

The sense strand or antisense strand of the siRNA according to the present invention may bind to the sequences of serotypes 1, 2, 3 and 4 of dengue virus.

The dengue virus-specific siRNA according to the present invention has a nucleotide sequence designed such that it can bind complementary to an mRNA encoding the gene of interest, and thus it can effectively inhibit the expression of the gene of interest. Also, the 3' end of the siRNA may comprise an overhang having one or two or more unpaired nucleotides.

In addition, the siRNA may comprise various chemical modifications for imparting nuclease resistance and reducing non-specific immune responses in order to increase the in vivo stability thereof.

A modification of the first or second oligonucleotide of the siRNA according to the present invention may be one modification or a combination of two or more modifications selected from among: modification in which an OH group at the 2' carbon position of a sugar structure in one or more nucleotides is substituted with —CH$_3$ (methyl), —OCH$_3$ (methoxy), —NH$_2$, —F (fluorine), —O-2-methoxyethyl-O-propyl, —O-2-methylthioethyl, —O-3-aminopropyl, —O-3-dimethylaminopropyl, —O—N-methylacetamido or —O— dimethylamidooxyethyl; modification in which oxygen in a sugar structure in nucleotides is substituted with sulfur; modification of a bond between nucleotides to a phosphorothioate, boranophosphophate or methyl phosphonate bond; and modification to PNA (peptide nucleic acid), LNA (locked nucleic acid) or UNA (unlocked nucleic acid) (Ann. Rev. Med. 55, 61-65 2004; U.S. Pat. No. 5,660,985; U.S. Pat. No. 5,958,691; U.S. Pat. No. 6,531,584; U.S. Pat. No. 5,808,023; U.S. Pat. No. 6,326,358; U.S. Pat. No. 6,175,001; Bioorg. Med. Chem. Lett. 14:1139-1143, 2003; RNA, 9:1034-1048, 2003; Nucleic Acid Res. 31:589-595, 2003; Nucleic Acids Research, 38(17) 5761-5773, 2010; Nucleic Acids Research, 39(5) 1823-1832, 2011).

The dengue virus-specific siRNA according to the present invention reduces the expression of the gene of interest and significantly reduces the expression of the protein of interest, thereby inhibiting the release of progeny virus into a cell culture medium.

In another aspect, the present invention provides a conjugate in which a hydrophilic compound and a hydrophobic compound are conjugated to both ends of the dengue virus-specific siRNA in order to ensure the efficient in vivo delivery of the siRNA and increase the stability of the siRNA.

The siRNA conjugate comprising the hydrophilic compound and hydrophobic compound conjugated to the siRNA as described above forms self-assembled nanoparticles by the hydrophobic interaction of the hydrophobic compound moieties (see Korean Patent Registration No. 1224828). This conjugate has advantages in that it has very high in vivo delivery efficiency and in vivo stability, and also has a uniform particle size distribution, and thus the quality control (QC) thereof is easy so that a process for preparing a drug from the conjugate is simple.

In a preferred embodiment, a double-stranded oligo RNA structure comprising the dengue virus-specific siRNA according to the present invention preferably has a structure represented by the following structural formula (1):

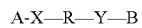   Structural formula (1)

wherein A represents a hydrophilic compound, B represents a hydrophobic compound, X and Y each independently represents a simple covalent bond or a linker-mediated covalent bond, and R represents a dengue virus-specific siRNA.

More preferably, the double-stranded oligo RNA structure comprising the dengue virus-specific siRNA according to the present invention preferably has a structure represented by the following structural formula (2):

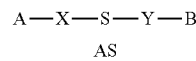   Structural formula (2)

wherein A, B, X and Y are as defined in structural formula (1) above, S represents the sense strand of the dengue virus-specific siRNA, and AS represents the antisense strand of the dengue virus-specific siRNA.

More preferably, the double-stranded oligo RNA structure comprising the dengue virus-specific siRNA has a structure represented by the following formula (3) or (4):

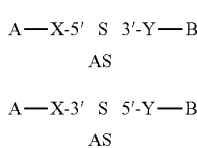

wherein A, B, S, AS, X and Y are as defined in structural formula (1) above, and 5' and 3' represent the 5' end and 3' end of the sense strand of the dengue virus-specific siRNA.

It will be obvious to those skilled in the art that one to three phosphate groups may be bound to the 5' end of the antisense strand of the double-stranded oligo RNA structure comprising the dengue virus-specific siRNA as shown in structural formula (1) to structural formula (4) and that shRNA may be used in place of the siRNA.

The hydrophilic compound in structural formula (1) to structural formula (4) above is preferably a cationic or nonionic polymer compound having a molecular weight of 200-10,000, and more preferably a nonionic polymer compound having a molecular weight of 1,000-2,000. For example, the hydrophilic polymer compound that is used in the present invention is preferably a nonionic hydrophilic polymer compound such as polyethylene glycol, polyvinyl pyrrolidone or polyoxazoline, but is not limited thereto.

Particularly, the hydrophilic compound (A) in structural formula (1) to structural formula (4) may be used in the form of hydrophilic blocks as shown in the following structural formula (5) or (6), and a suitable number (n in structural formula (5) or (6)) may be used as required, thereby overcoming the problems associated with polydisperse properties that may occur when general synthetic polymer compounds:

$(A'_m\text{-}J)_n$     Structural formula (5)

$(J\text{-}A'_m)_n$     Structural formula (6)

wherein A' represents a hydrophilic monomer, J represents a linker that connects between a number (m) of hydrophilic monomers or connects a number (m) of hydrophilic monomers with siRNA, m is an integer ranging from 1 to 15, n is an integer ranging from 1 to 10, and a repeat unit represented by $(A'_m\text{-}J)$ or $(J\text{-}A_m')$ corresponds to the basic unit of the hydrophilic block.

If the hydrophilic block as shown in structural formula (5) or (6) above is used, the double-stranded oligo RNA structure comprising the dengue virus-specific siRNA according to the present invention may have a structure as shown in the following structural formula (7) or (8):

$(A'_m\text{-}J)_n\text{-}X\text{—}R\text{—}Y\text{—}B$    Structural formula (7)

$(J\text{-}A'_m)_n\text{-}X\text{—}R\text{—}Y\text{—}B$    Structural formula (8)

wherein X, R, Y and B are as defined in structural formula (1) above, and A', J, m and n are as defined in structural formula (5) and (6) above.

As the hydrophilic monomer (A') in structural formula (5) to structural formula (8) above, one selected from among nonionic hydrophilic polymers may be used without limitation, as long as it coincides with the purpose of the present invention. Preferably, a monomer selected from among compound (1) to compound (3) set forth in Table 1 below may be used. More preferably, a monomer of compound (1) may be used. In compound (1), G may preferably be selected from among $CH_2$, O, S and NH.

Particularly, among hydrophilic monomers, the monomer represented by compound (1) is very suitable for the preparation of the structure according to the present invention, because it has advantages in that it can introduce various functional groups, has good biocompatibility to induce less immune responses, can increase the in vivo stability of the siRNA included in the structure represented by structural formula (7) or (8), and can increase the delivery efficiency of the siRNA.

TABLE 1

Structure of hydrophilic monomers used in the present invention

| | |
|---|---|
| 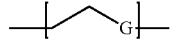<br>G is $CH_2$, O, S or NH | Compound (1) |
| 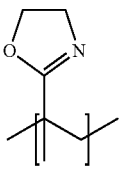 | Compound (2) |
| 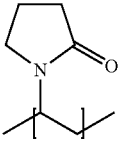 | Compound (3) |

The total molecular weight of the hydrophilic compound (hydrophilic compound block) in structural formula (5) to structural formula (8) is preferably in the range of 1,000 to 2,000. Thus, for example, when compound (1) in structural formula (7) and structural formula (8) is hexaethylene glycol that is a compound in which G is O and m is 6, the repeat number (n) is preferably 3 to 5, because the hexaethylene glycol space has a molecular weight of 344.

Particularly, the present invention is characterized in that a suitable number (represented by n) of repeat units of the hydrophilic group (hydrophilic blocks) represented by $(A'_m\text{-}J)$ or $(J\text{-}A'_m)_n$ in structural formula (5) and structural formula (6) may be used as required. The hydrophilic monomer J and linker J included in each hydrophilic block may be the same or different between the hydrophilic blocks. In other words, when 3 hydrophilic blocks are used (n=3), the hydrophilic monomer of compound (1), the hydrophilic monomer of compound (2) and the hydrophilic monomer of compound (3) may be used in the first, second and third blocks, respectively, suggesting that different monomers may be used in all hydrophilic blocks. Alternatively, any one selected from the hydrophilic monomers of compounds (1) to (3) may also be used in all the hydrophilic blocks. Similarly, as the linker that mediates the bonding of the hydrophilic monomer, the same linker may be used in the hydrophilic blocks, or different linkers may be used in the hydrophilic blocks. In addition, m that is the number of the hydrophilic monomers may also be the same or different between the hydrophilic blocks. In other words, in the first hydrophilic block, three hydrophilic monomers are connected (m=3), and in the second hydrophilic block, five hydrophilic monomers are connected (m=5), and in the third hydrophilic block, four hydrophilic monomers are connected (m=4), suggesting that different numbers of the hydrophilic monomers may be used in the hydrophilic blocks. Alternatively, the same number of the hydrophilic monomers may also be used in all the hydrophilic blocks.

In addition, in the present invention, the linker (J) is preferably selected from the group consisting of $PO_3^-$, $SO_3$ and $CO_2$, but is not limited thereto. It will be obvious to those skilled in the art that any linker selected depending on the hydrophilic monomer used may be used, as long as it coincides with the purpose of the present invention.

The hydrophobic compound (B) in structural formula (1) to structural formula (4), structural formula (7) and structural formula (8) functions to form nanoparticles made of the oligonucleotide structure as shown in structural formula (1) to structural formula (4), structural formula (7) and structural formula (8) by hydrophobic interactions. The hydrophobic compound preferably has a molecular weight of 250-1,000, and may be a steroid derivative, a glyceride derivative, glycerol ether, polypropylene glycol, a $C_{12}$-$C_{50}$ unsaturated or saturated hydrocarbon, diacylphosphatidylcholine, fatty acid, phospholipid, lipopolyamine or the like, but is not limited thereto. It will be obvious to those skilled in the art that any hydrophobic compound may be used, as long as it coincides with the purpose of the present invention.

The steroid derivative may be selected from the group consisting of cholesterol, cholestanol, cholic acid, cholesteryl formate, cholestanyl formate, and cholesteryl amine, in which the glyceride derivative may be selected from mono-, di-, and tri-glycerides, and the like. Herein, fatty acid of the glyceride is preferably $C_{12}$-$C_{50}$ unsaturated or saturated fatty acid.

Particularly, among the hydrophobic compounds, the saturated or unsaturated hydrocarbon or cholesterol is preferably used, because it can be easily bound in a process of synthesizing the oligonucleotide structure according to the present invention. Most preferably, a $C_{24}$ hydrocarbon, particularly tetradocosane containing a disulfide bond is used.

The hydrophobic compound may be bound to the distal end of the hydrophilic compound, and may be bound to any position of the sense or antisense strand of the siRNA.

The hydrophilic compound or hydrophobic compound in structural formulas (1) to (4), (7) and (8) according to the present invention is bound to the dengue virus-specific siRNA by a single covalent bond or a linker-mediated covalent (X or Y). The linker that mediates the covalent bond is covalently bound to the hydrophilic or hydrophobic compound at the end of the dengue virus-specific siRNA, and is not specifically limited as long as it provides a degradable bond in a specific environment, if required. Therefore, the linker that is used in the present invention may be any compound that is bound in order to activate the dengue virus-specific siRNA and/or the hydrophilic (or hydrophobic) compound in the process of preparing the double-stranded oligo RNA structure according to the present invention. The covalent bond may be any one of a non-degradable bond and a degradable bond. Herein, examples of the non-degradable bond include, but are not limited to, an amide bond and a phosphate bond, and examples of the degradable bond include, but are not limited to, a disulfide bond, an acid-degradable bond, an ester bond, an anhydride bond, a biodegradable bond, and an enzyme-degradable bond.

As the siRNA represented by R (or S and AS) in structural formulas (1) to (4), (7) and (8), any siRNA having the property of binding specifically to dengue virus may be used without limitation. Preferably, the siRNA that is used in the present invention comprises a sense strand comprising any one sequence selected from among SEQ ID NO: 1 to SEQ ID NO: 88, and an antisense strand having a sequence complementary to that of the sense strand.

The siRNA according to the present invention preferably comprises a dengue virus-specific siRNA sense strand having a sequence set forth in any one of SEQ ID NOS: 4 to 8, 13, 16, 20, 22, 23, 29, 32, 34, 39 to 42, 44 to 47, 51, 52, 70 to 72, 76, 77 and 80 to 82. More preferably, it comprises a dengue virus-specific siRNA sense strand having a sequence set forth in any one of SEQ ID NOS: 4, 16, 22, 51, 52, 71 and 82. Most preferably, it comprises a dengue virus-specific siRNA sense strand having a sequence set forth in any one of SEQ ID NOS: 51, 52, 71 and 82.

In the double-stranded oligo RNA structure comprising the dengue virus-specific siRNA according to the present invention, an amine or polyhistidine group may additionally be introduced into the distal end of the hydrophilic compound bound to the siRNA in the structure.

This facilitates the intracellular uptake and endosomal escape of a carrier comprising the double-stranded oligo RNA structure comprising the dengue virus-specific siRNA according to the present invention, and it has been already reported that the introduction of an amine group and a polyhistidine group can be used to facilitate the intracellular introduction and endosomal escape of carriers such as quantum dots, dendrimers or liposome.

Specifically, it is known that a primary amine group introduced into the end or outside of a carrier is protonated at biological pH while forming a conjugate by interaction with a negatively charged gene, and that endosomal escape is facilitated due to an internal tertiary amine having a buffering effect at low pH after intracellular uptake, and thus the carrier can be protected from lysosomal degradation (inhibition of gene delivery and expression using a polymer-based hybrid material, *Polymer Sci. Technol.*, Vol. 23, No. 3, pp 254-259).

Also, it is known that histidine, a non-essential amino acid, has an imidazole ring (pKa=6.04) at the residue (—R), and thus has the effect of increasing buffering capacity in endosome and lysosome, and thus histidine modification may be used in non-viral gene carriers, including liposome, in order to increase endosomal escape efficiency (Novel histidine-conjugated galactosylated cationic liposomes for efficient hepatocyte selective gene transfer in human hepatoma HepG2 cells. J. Controlled Release 118, pp 262-270).

The amine group or polyhistidine group may be connected to the hydrophilic compound or the hydrophilic block by one or more linkers.

When the amine group or polyhistidine group is introduced into the hydrophilic compound of the double-stranded oligo RNA structure represented by structural formula (1) according to the present invention, the RNA structure may have a structure as shown in the following structural formula (9):

$$P-J_1-J_2-A-X—R—Y—B \qquad \text{Structural formula (9)}$$

wherein A, B, R, X and Y are as defined in structural formula (1) above, P represents an amine group or polyhistidine group, and $J_1$ and $J_2$ are linkers and may be each independently selected from among a simple covalent bond, $PO_3^-$, $SO_3$, $CO_2$, a $C_{2-12}$ alkyl, alkenyl and alkinyl, but are not limited thereto. It will be obvious skilled in the art that any linker may be used as $J_1$ and $J_2$, as long as it coincides with the purpose of the present invention.

Preferably, when an amine group is introduced, $J_2$ is a simple covalent bond or $PO_3^-$, and $J_1$ is a $C_6$ alkyl, but are not limited thereto.

In addition, when a polyhistidine group is introduced, it is preferred that $J_2$ in structural formula (9) is a simple covalent bond or $PO_3^-$, and $J_1$ is compound (4), but are not limited thereto.

$$C_{2\text{-}12}\ \text{Alkyl}—NH—\overset{O}{\underset{\|}{C}}—\text{cyclohexyl-CH}_2\text{-cyclopentyl} \qquad \text{Compound (4)}$$

In addition, when the hydrophilic compound of the double-stranded oligo RNA structure as shown in structural formula (9) is the hydrophilic block represented by structural formula (5) or (6) and is introduced with an amine group or a polyhistidine group, the RNA structure may have a structure as shown in the following structural formula (10) or (11):

$$P\text{-}J_1\text{-}J_2\text{-}(A'_m\text{-}J)_n\text{-}X—R—Y—B \qquad \text{Structural formula (10)}$$

$$P\text{-}J_1\text{-}J_2\text{-}(J\text{-}A'_m)_n\text{-}X—R—Y—B \qquad \text{Structural formula (11)}$$

wherein X, R, Y, B, A', J, m and n are as defined in structural formula (5) or (6) above, and P, $J_1$ and $J_2$ are as defined in structural formula (9).

Particularly, the hydrophilic compound in structural formula (10) and structural formula (11) is preferably bound to the 3' end of the sense strand of the dengue virus-specific siRNA, and in this case, structural formula (9) to structural formula (11) may correspond to the following structural formula (12) to structural formula (14):

$$P—J_1—J_2—A—X\text{-}3'\ S\ 5'\text{-}Y—B \qquad \text{Structural formula (12)}$$
$$AS$$

$$P—J_1—J_2—(A'_m—J)_n—X\text{-}3'\ S\ 5\text{-}Y—B \qquad \text{Structural formula (13)}$$
$$AS$$

$$P—J_1—J_2—(J—A'_m)_n—X\text{-}3'\ S\ 5'\text{-}Y—B \qquad \text{Structural formula (14)}$$
$$AS$$

wherein X, R, Y, B, A, A' J, m, n. P, $J_1$ and $J_2$ are as defined in structural formula (9) to structural formula (11) above, and 5' and 3' represent the 5' end and 3' end of the sense strand of the dengue virus-specific siRNA.

An amine group that may be used in the present invention may be a primary, secondary or tertiary amine group. Preferably, a primary amine group is used. The introduced amine group may be an amine salt. For example, a salt of the primary amine group may be present as $NH_3^+$.

In addition, a polyhistidine group that may be used in the present invention preferably comprises 3 to 10 histidines, more preferably 5 to 8 histidines, and most preferably six histidines. In addition to histidines, one or more cysteines may be included.

Active targeting using nanoparticles is a technology of binding a targeting moiety to nanoparticles, and it has been reported that the active targeting promotes preferential accumulation of nanoparticles in the target tissue or improves internalization of nanoparticles into the target cells (Does a targeting ligand influence nanoparticle tumor localization or uptake Trends Biotechnol. 2008 October; 26(10):552-8. Epub 2008 Aug. 21). The active targeting is performed using a targeting moiety capable of binding a target cell surface-specific or overexpressed carbohydrate, receptor, or antigen (Nanotechnology in cancer therapeutics: bioconjugated nanoparticles for drug delivery. Mol Cancer Ther 2006; 5(8): 1909-1917).

Thus, when a targeting moiety is included in the double-stranded oligo RNA structure comprising the dengue virus-specific siRNA according to the present invention and nanoparticles formed therefrom, it can promote the efficient delivery of the RNA structure into target cells so that the RNA structure can be delivered into the target cells even at a relatively low concentration to exhibit a high effect of regulating the expression of the target gene, and the non-specific delivery of the dengue virus-specific siRNA into other organs and cells can be prevented.

Accordingly, the present invention provides a double-stranded oligo RNA structure in which a ligand (L), particularly a ligand having the property of binding specifically to a receptor that enhances target cell internalization by receptor-mediated endocytosis (RME), is further bound to the structure represented by any one of structural formulas (1) to (4), (7) and (8). For example, a structure comprising a ligand bound to the double-stranded RNA structure represented by structural formula (1) has a structure as shown in the following structural formula (15):

$$(L_I\text{-}Z)\text{-}A\text{-}X—R—Y—B \qquad \text{Structural formula (15)}$$

wherein A, B, X and Y are as defined in structural formula (1) above, L is a ligand having the property of binding specifically to a receptor that enhances target cell internalization by receptor-mediated endocytosis (RME), Z represents a simple covalent bond or a linker that mediates the binding between the ligand and the hydrophilic monomer in the hydrophilic block, and I is an integer ranging from 1 to 5, and preferably from 1 to 3.

The ligand in structural formula (15) may preferably be selected from among: target receptor-specific antibodies, aptamers and peptides, which have the RME property of enhancing target cell internalization; folate (the term "folate" is generally used interchangeably with folic acid, and the term "folate" as used herein means folate that is a natural form or is activated in the human body); and chemical compounds, including hexoamine such as N-acetyl galactosamine (NAG), and saccharides or carbohydrates such as glucose and mannose, but is not limited thereto.

In addition, the hydrophilic compound A in structural formula (15) above may be used in the form of the hydrophilic block represented by structural formula (5) or (6).

In another aspect, the present invention provides a method for preparing the double-stranded oligo RNA structure comprising the dengue virus-specific siRNA.

For example, the method for preparing the double-stranded oligo RNA structure comprising the dengue virus-specific siRNA may comprise the steps of:

(1) binding a hydrophilic compound to a solid support;
(2) synthesizing a RNA single strand on the hydrophilic compound-bound solid support;
(3) covalently binding a hydrophobic compound to the 5' end of the RNA single strand;
(4) synthesizing a RNA single strand having a sequence complementary to the sequence of the RNA single strand of step (3);
(5) separating and purifying a RNA-polymer structure and the RNA single strand from the solid support after completion of the synthesis; and
(6) annealing the prepared RNA-polymer structure with the RNA single strand having the complementary sequence.

The solid support that is used in the present invention is preferably controlled pore glass (CPG), but is not limited thereto, polystyrene, silica gel, cellulose paper or the like may also be used. If CPG is used, it preferably has a diameter of 40-180 μm and a pore size of 500-3000 Å. After step (5), the molecular weights of the prepared and purified RNA-polymer structure and RNA single strand can be measured by a MALDI-TOF mass spectrometer in order to confirm whether the desired RNA-polymer structure and RNA single strand were prepared. In the above-described preparation method, step (4) of synthesizing the RNA single strand having a sequence complementary to the sequence of the RNA single strand synthesized in step (2) may be performed before step (1) or during any one step of steps (1) to (5).

In addition, the RNA single strand having a sequence complementary to the sequence of the RNA single strand synthesized in step (2) may be used in a state in which a phosphate group is bound to the 5' end of the RNA single strand.

Meanwhile, the present invention provides a method for preparing a double-stranded oligo RNA structure further comprising a ligand bound to the double-stranded oligo RNA structure comprising the dengue virus-specific siRNA.

For example, the ligand-bound oligo RNA structure comprising the dengue virus-specific siRNA may comprise the steps of:
(1) binding a hydrophilic compound to a solid support having a functional group bound thereto;
(2) synthesizing a RNA single strand on the solid support having the functional group and hydrophilic compound bound thereto;
(3) covalently binding a hydrophobic compound to the 5' end of the RNA single strand;
(4) synthesizing a RNA single strand having a sequence complementary to the sequence of the RNA single strand synthesized in step (2);
(5) separating the functional group-RNA-polymer structure and the RNA single strand having the complementary sequence from the solid support after completion of the synthesis;
(6) binding a ligand to the end of the hydrophilic compound by the functional group to prepare a ligand-RNA-polymer structure single strand; and
(7) annealing the prepared ligand-RNA-polymer structure with the RNA single strand having the complementary sequence.

After step (6), the prepared the prepared ligand-RNA-polymer structure and the RNA single strand having the complementary sequence may be separated and purified, and then the molecular weights thereof may be measured by a MALDI-TOF mass analyzer in order to confirm whether the desired ligand-RNA-polymer structure and the desired RNA single strand having the complementary sequence were prepared. By annealing the prepared ligand-RNA-polymer structure with the RNA single strand having the complementary sequence, a ligand-double stranded oligo RNA structure can be prepared. In the above-described preparation method, step (4) of synthesizing the RNA single strand having a sequence complementary to the sequence of the RNA single strand synthesized in step (3) may be performed before step (1) or during any one step of steps (1) to (6).

In still another aspect, the present invention provides nanoparticles comprising the double-stranded oligo RNA structure comprising the dengue virus-specific siRNA.

As described above, the double-stranded oligo RNA structure comprising the dengue virus-specific siRNA is an amphiphilic structure comprising both the hydrophobic compound and the hydrophilic compound, in which the hydrophilic moiety is oriented toward of the structure by interactions (such as hydrogen bonds) with water molecules in vivo, and the hydrophobic compound moieties are oriented toward the inside of the structure by hydrophobic interactions therebetween to thereby form thermodynamically stable nanoparticles. In other words, the hydrophobic compound is located in the center of the nanoparticles, and the hydrophilic compound is located on the outside of the dengue virus-specific siRNA to cover the dengue virus-specific siRNA, thereby forming nanoparticles. The nanoparticles formed as described above enhance the intracellular delivery of the dengue virus-specific siRNA and enhances siRNA efficiency.

The nanoparticles according to the present invention is characterized in that they are composed of the double-stranded oligo RNA structure comprising siRNAs having different sequences. It is understood that the siRNAs having different sequences in the present invention may be other target gene-specific siRNAs of dengue virus and may have different sequences while the same target gene specificity.

In addition, the nanoparticles according to the present invention may also include a double-stranded oligo RNA structure target gene-specific siRNAs for disease treatment other than the dengue virus-specific siRNA.

In still another aspect, the present invention provides a composition for the inhibition of dengue virus replication and a pharmaceutical composition for the prevention and/or treatment of dengue virus infection, which comprise the dengue virus-specific siRNA, the double-stranded oligo RNA structure comprising the same, and/or nanoparticles comprising the double-stranded oligo RNA structure.

Particularly, the composition for inhibiting dengue virus replication, which comprises the double-stranded oligo RNA structure according to the present invention, may comprise a double-stranded oligo RNA structure comprising a dengue virus-specific siRNA comprising a sense strand having any one sequence selected from the sequences of SEQ ID NOS: 4 to 8, 13, 16, 20, 22, 23, 29, 32, 34, 39 to 42, 44 to 47, 51, 52, 70 to 72, 76, 77 and 80 to 82, preferably any one sequence selected from among the sequences of SEQ ID NOS: 4, 16, 22, 51, 52, 71 and 82, and most preferably any one sequence selected from among the sequences of SEQ ID NOS: 51, 52, 71 and 82, and an antisense strand having a sequence complementary to the sequence of the sense strand. In addition, it may comprise a mixture of the double-stranded oligo RNA structures comprising the dengue virus-specific siRNAs.

When the composition for inhibiting dengue virus replication comprises two or more different double-stranded oligo RNA structures having the dengue virus-specific siRNAs having different sequences as described above, it can exhibit a synergistic effect, like combination therapy.

In addition, the nanoparticles in the pharmaceutical composition comprising the nanoparticles composed of the double-stranded oligo RNA structure according to the present invention may be composed of only anyone structure selected from among double-stranded oligo RNA structures comprising the dengue virus-specific siRNAs, or may be composed of a mixture of two or more different double-stranded oligo RNA structures comprising the dengue virus-specific siRNAs.

The composition of the present invention may comprise, in addition to the active ingredient, one or more pharmaceutically acceptable carriers. The pharmaceutically acceptable carriers should be compatible with the active ingredient, and may be one selected from among physiological saline, sterile water, Ringer's solution, buffered saline, dextrose solution, maltodextrin solution, glycerol, ethanol, and a mixture of two or more thereof. If necessary, the composition may contain other conventional additives such as an antioxidant, a buffer or a bacteriostatic agent. In addition, a diluent, a dispersing agent, a surfactant, a binder and a lubricant may additionally be added to the composition to prepare injectable formulations such as an aqueous solution, a suspension and an emulsion. Particularly, the composition is preferably provided as a lyophilized formulation. For the preparation of a lyophilized formulation, a conventional method known in the technical field to which the present invention pertains may be used, and a stabilizer for lyophilization may also be added. Furthermore, the composition can preferably be formulated according to diseases or components by a suitable method known in the art or by a method disclosed in Remington's Pharmaceutical Science, Mack Publishing Company, Easton Pa.

The content of the active ingredient in the composition of the present invention and the method for administration of the composition can generally be determined by those skilled in the art based on the condition of the patient and the severity of the disease. In addition, the composition can be formulated in various forms, including powder, tablet, capsule, liquid, injectable solution, ointment and syrup formulations, and may be provided by use of a unit dosage form or multi-dosage container, for example, a sealed ampule or vial.

The composition of the present invention may be administered orally or parenterally. The composition according to the present invention may be administered, for example, orally, intravenously, intramuscularly, intraarterially, intramedullarily, intradually, intracardially, transdermally, subcutaneously, intraperitoneally, intrarectally, sublingually or topically, but is not limited thereto. The dose of the composition according to the present invention may vary depending on the patient's weight, age, sex, health condition and diet, the time of administration, the mode of administration, excretion rate, the severity of the disease, or the like, and can be easily determined by those skilled in the art. In addition, for clinical administration, the composition of the present invention may be prepared into a suitable formulation using a known technique.

In addition, the present invention provides a method for preventing or treating dengue virus infection, which comprises administering the double-stranded oligo RNA structure of the present invention or nanoparticles comprising the same to a patient in need of the prevention or treatment.

Advantageous Effects

The dengue virus-specific siRNA according to the present invention, the double-stranded oligo RNA structure comprising the same, and a composition for preventing or treating dengue virus infection, which comprises the double-stranded oligo RNA structure, can inhibit the expression of dengue virus with high efficiency without causing side effects, and thus can be very advantageously used for the prevention and treatment of dengue virus infection for which a suitable therapeutic agent is not currently present.

A: a graph showing the replication kinetics of dengue virus serotype 2;

B: a graph showing the replication kinetics of dengue virus serotype 3;

C: a graph showing the replication kinetics of dengue virus serotype 4.

Figure 3:
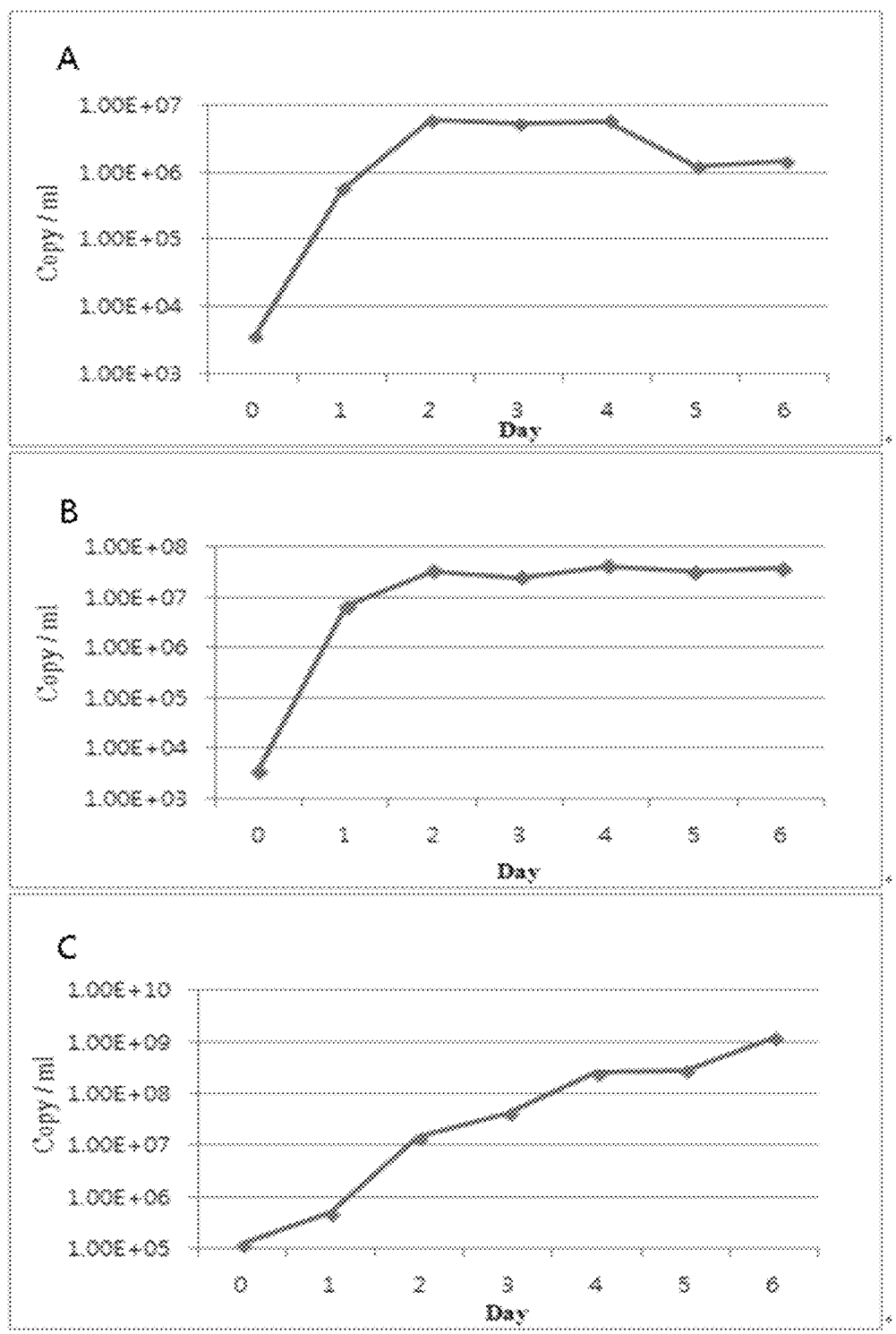

FIG. 3 is a set of graphs showing the replication kinetics of each serotype of dengue virus in a VeroE6 cell line.

A: a graph showing the replication kinetics of dengue virus serotype 2;

B: a graph showing the replication kinetics of dengue virus serotype 3;

C: a graph showing the replication kinetics of dengue virus serotype 4.

Figure 4:
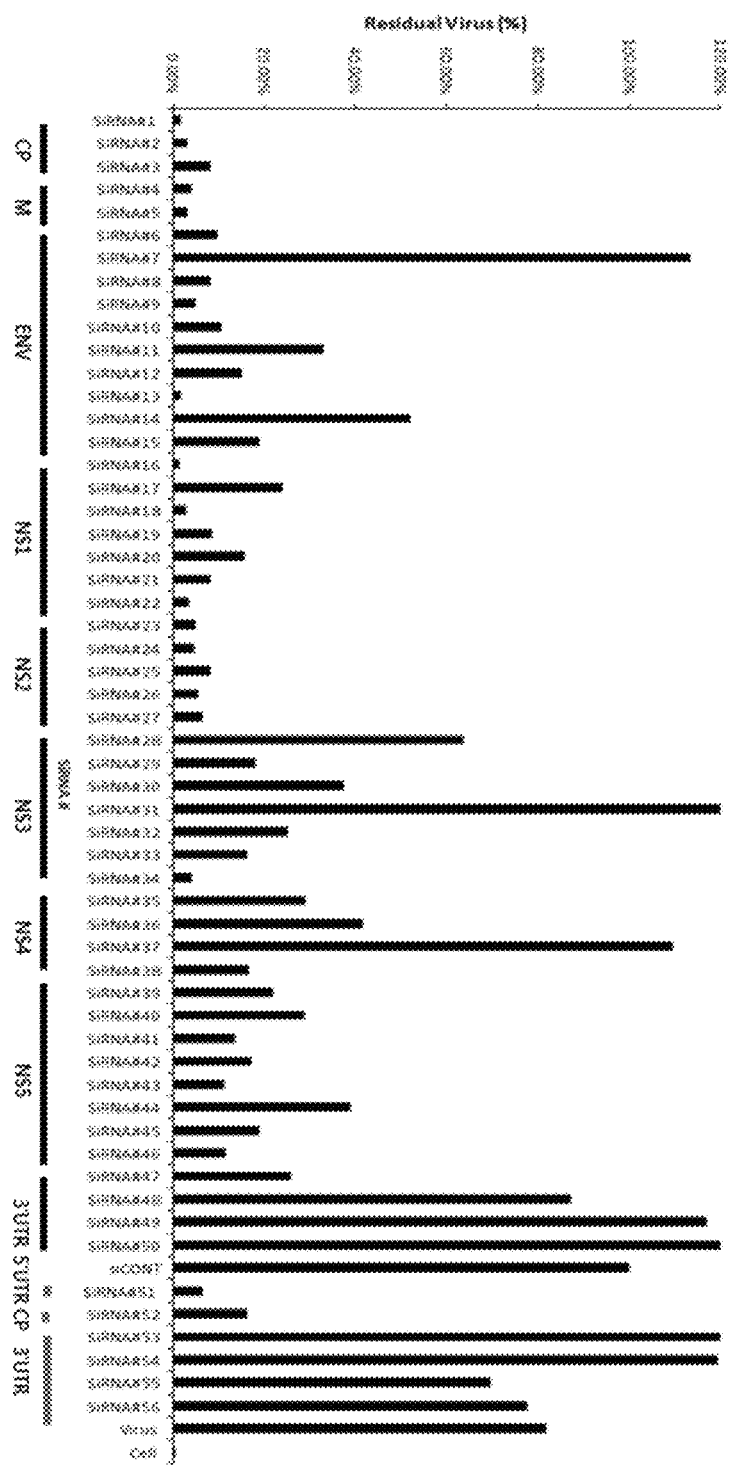

FIG. 4 shows the effects of primarily selected 56 siRNA candidates on the inhibition of replication of dengue virus serotype 4.

Figure 5:
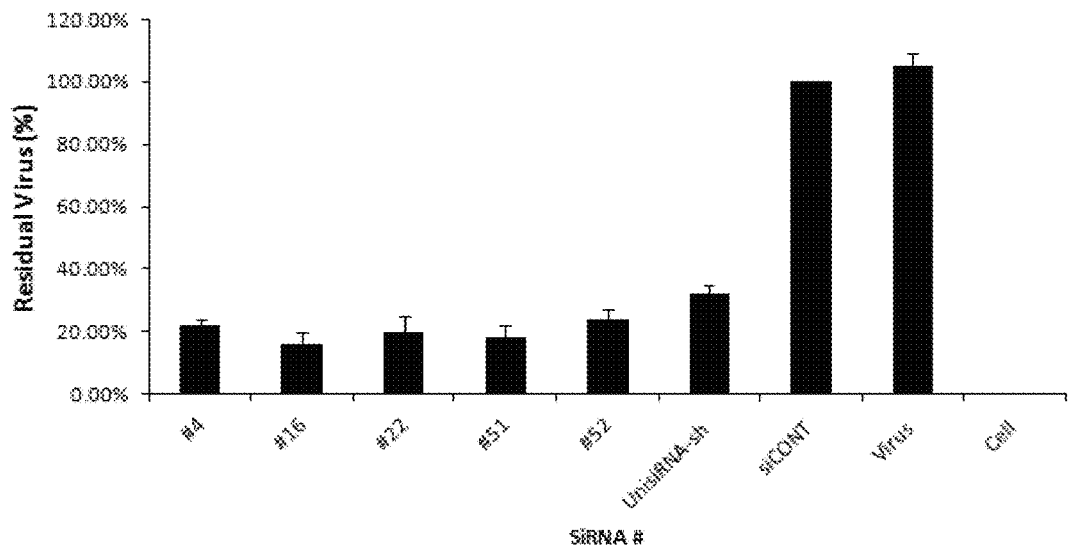

FIG. 5 shows the effects of primarily selected 5 siRNA candidates on the inhibition of replication of dengue virus serotype 4.

Figure 6:
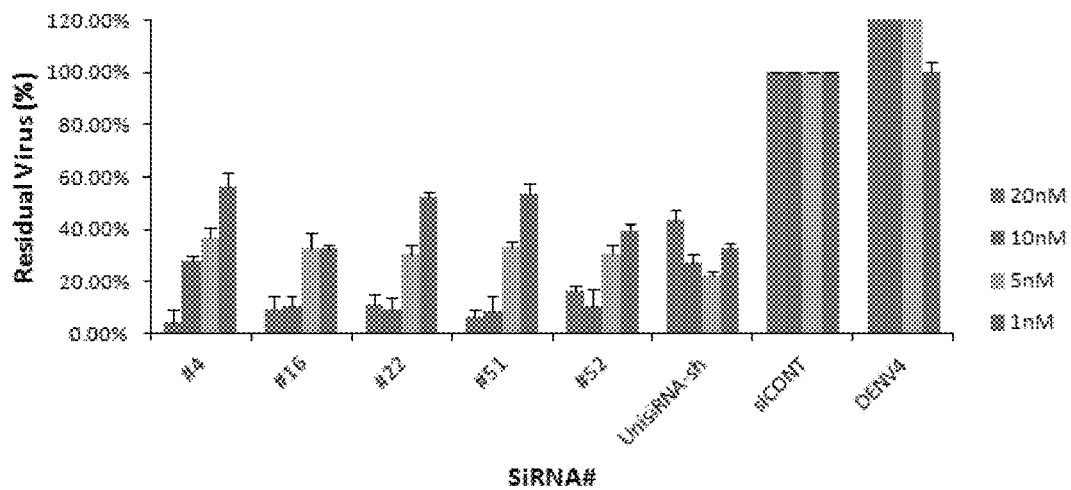

FIG. 6 shows the concentration-dependent effects of primarily selected 5 siRNA candidates on the inhibition of replication of dengue virus serotype 4.

Figure 7:
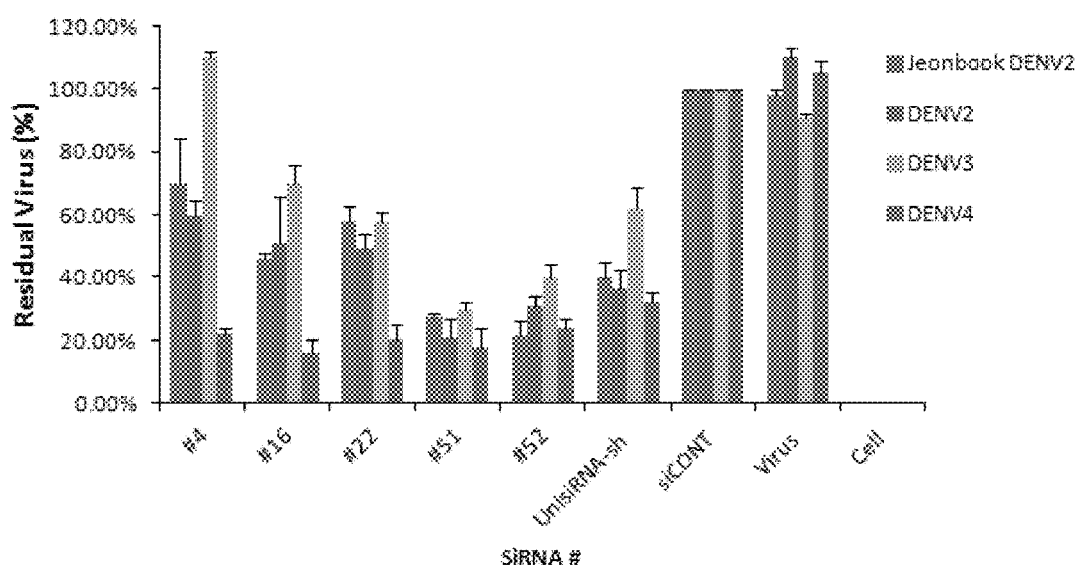

FIG. 7 shows the concentration-dependent effects of primarily selected 5 siRNA candidates on the inhibition of replication of each dengue virus serotype.

FIG. 8 shows the relative positions of secondary universal siRNAs designed by single nucleotide sliding window scanning from conventional universal SiRNA#51 and SiRNA#52 selected from a region showing high homology.

Figure 9A:
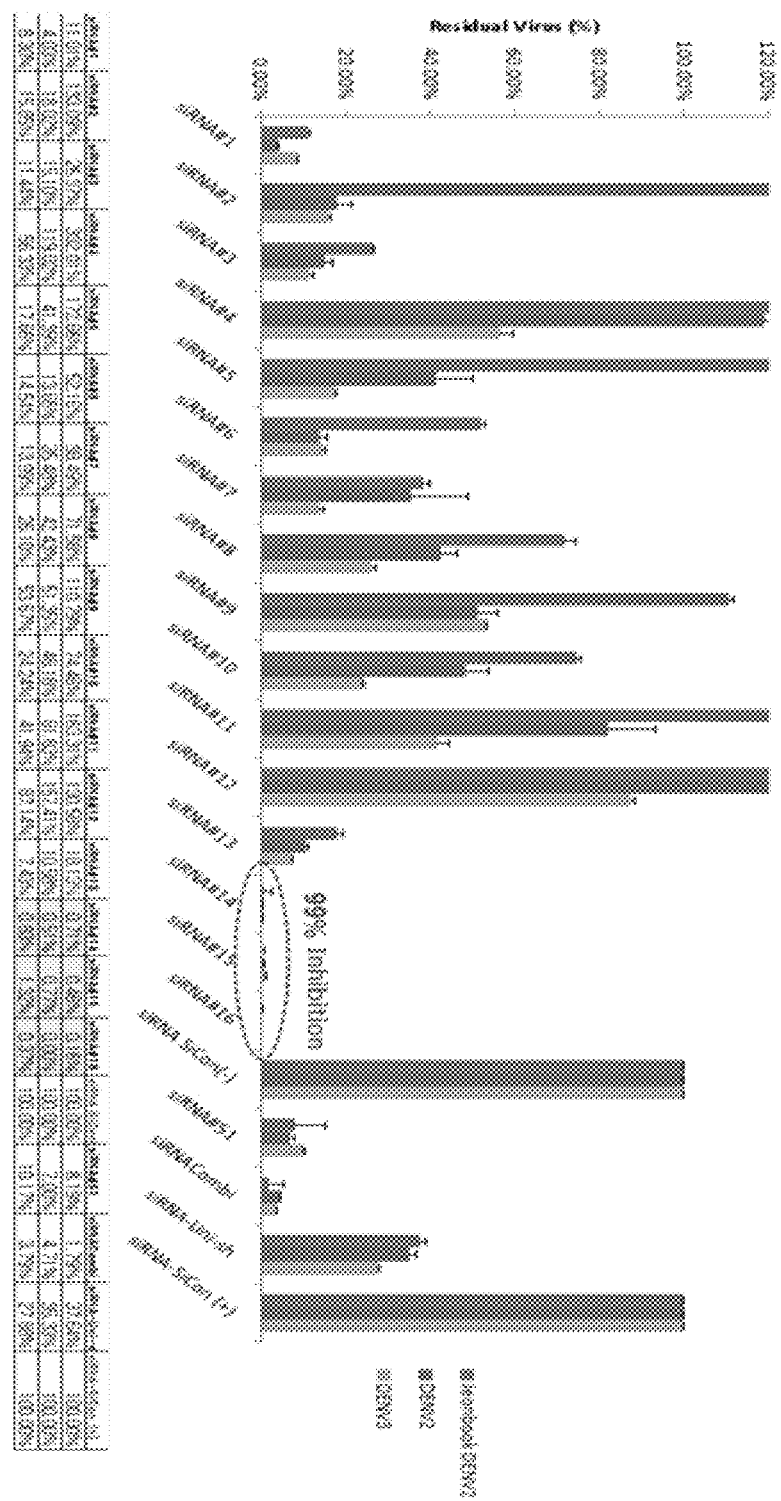
Figure 9B:
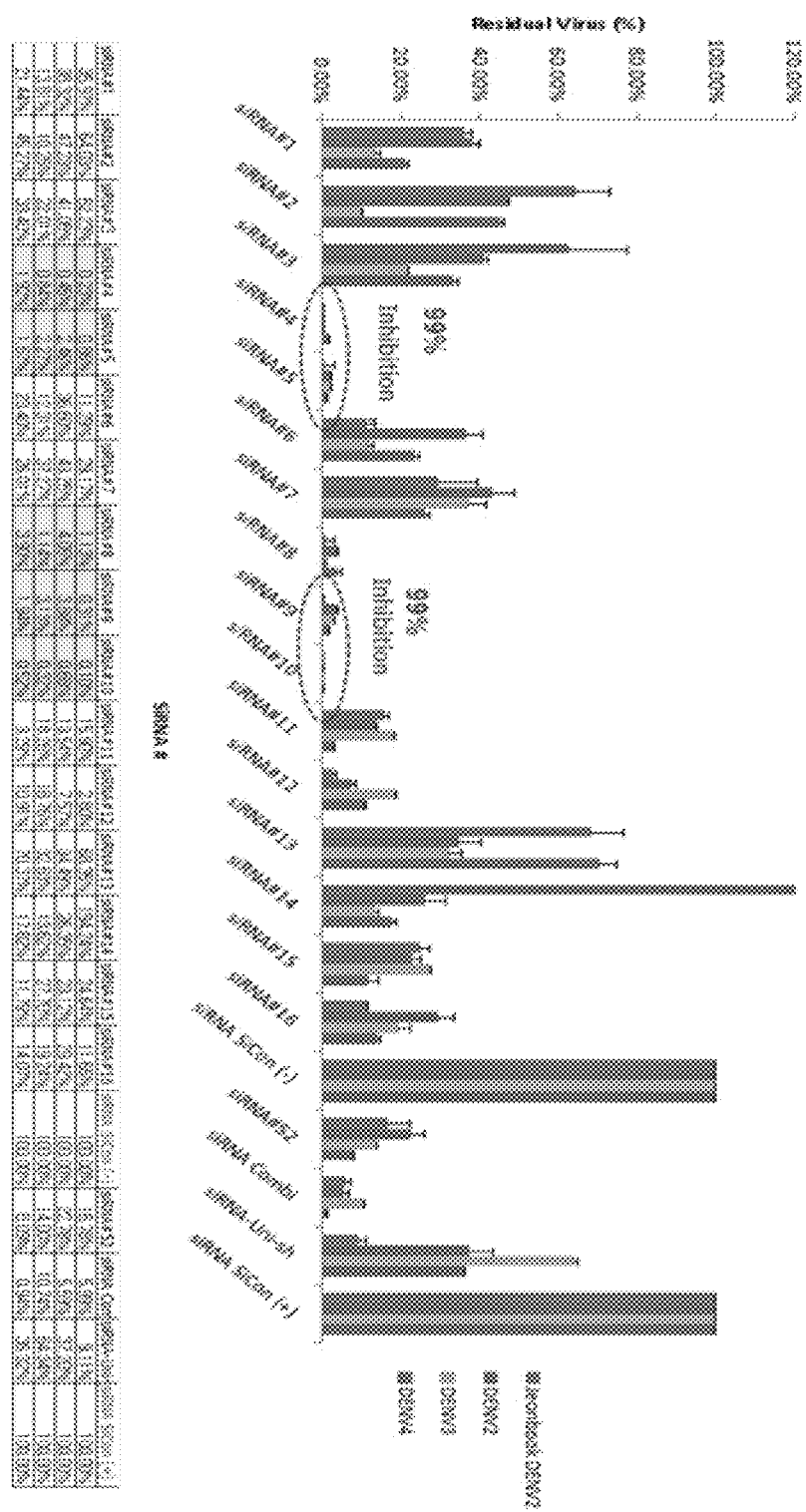

FIG. 9 is a set of graphs showing the dengue virus serotype 2 and serotype 3 replication inhibitory effects of secondary universal 32 siRNA candidates designed by single nucleotide sliding window scanning for primarily selected universal SiRNA#51 and SiRNA#52.

A: the replication inhibitory effects of SiRNA#51-based siRNAs;

B: the replication inhibitory effects of SiRNA#52-based siRNAs.

FIG. 10 is a set of graphs showing the inhibitory effects of finally selected two siRNAs (SiRNA#51-15 and SiRNA#52-10) on the replication of dengue virus serotype 2 to serotype 4.

A: the replication inhibitory effect of SiRNA#51-15;

B: the replication inhibitory effect of SiRNA#52-10.

FIG. 11 is a graph showing the inhibitory effects of a combination of finally selected two siRNAs (SiRNA#51-15 and SiRNA#52-10) on the replication of dengue virus serotype 2 to serotype 4 and dengue virus JB2.

FIG. 12 is a graph showing the inhibitory effects of a combination of finally selected two siRNAs (SiRNA#51-15 and SiRNA#52-10) on the replication of dengue virus serotype 2 to serotype 4 and dengue virus JB2 in a pre-virus infection condition in order to verify the possibility of actual application of the siRNAs for the treatment of dengue patients.

Figure 13:
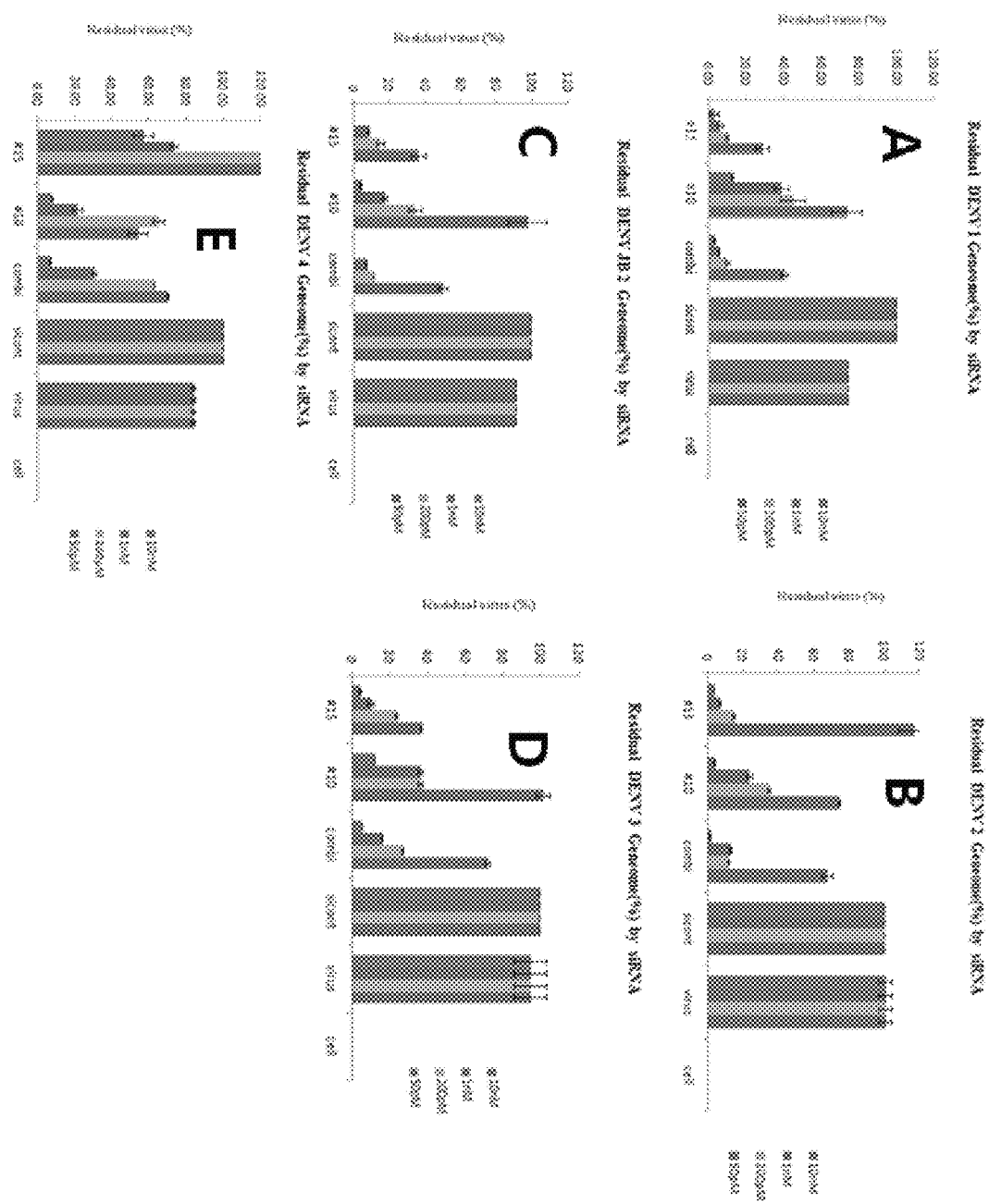

FIG. 13 is a set of graphs showing the concentration-dependent effects of finally selected two siRNAs (SiRNA#51-15 and SiRNA#52-10) on the replication of dengue virus serotype 1 to serotype 4 and dengue virus JB2 when the siRNAs were used alone or in combination.

A: dengue virus serotype 1;
B: dengue virus serotype 2;
C: dengue virus JB2;
D: dengue virus serotype 3;
E: dengue virus serotype 4.

FIG. 14 is a schematic view of a nanoparticle comprising the double-stranded oligo polymer structure according to the present invention.

Figure 15:
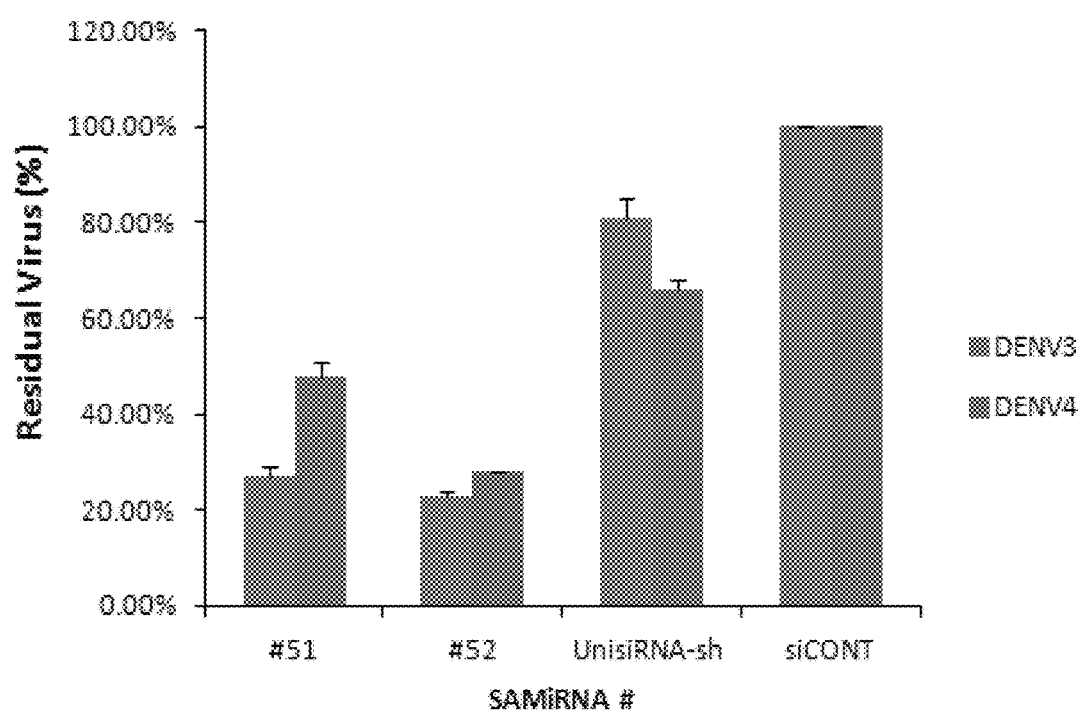

FIG. 15 shows the inhibitory effects of a SAMiRNA comprising a U1 siRNA according to the present invention on the replication of dengue virus serotype 4.

Figure 16:
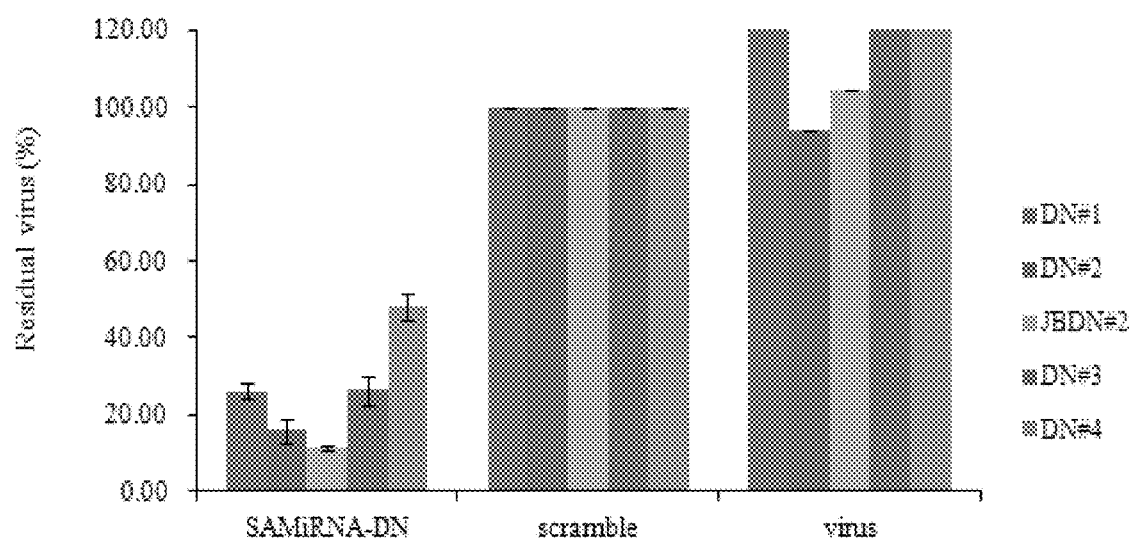

FIG. 16 is a graph showing the inhibitory effects of a Mono-HEG-SAMiRNA comprising a combi-siRNA according to the present invention on the replication of dengue virus serotypes 1 to 4 and dengue virus JB2.

Figure 17:
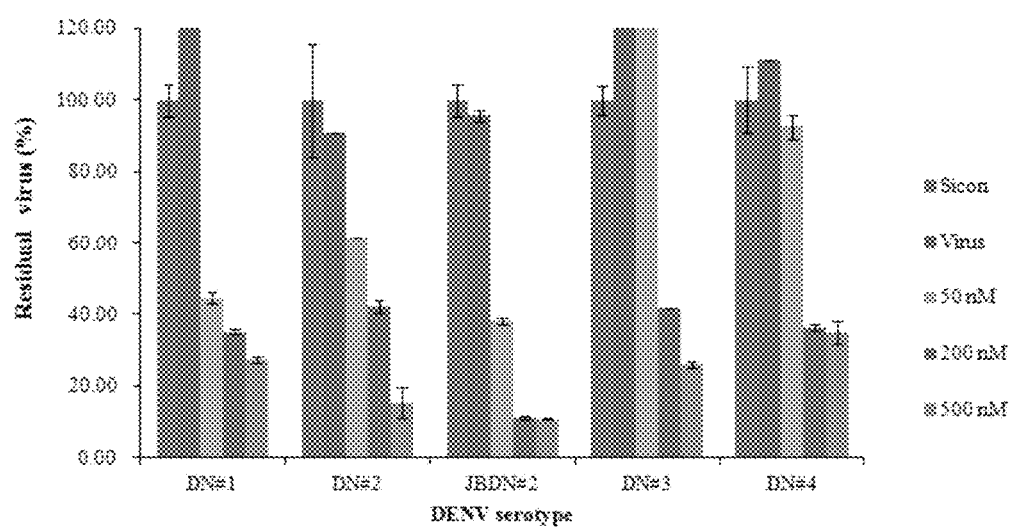

FIG. 17 is a graph showing the concentration-dependent inhibitory effects of a Mono-HEG-SAMiRNA comprising a combi-siRNA according to the present invention on the replication of dengue virus serotypes 1 to 4 and dengue virus JB2.

Figure 18:
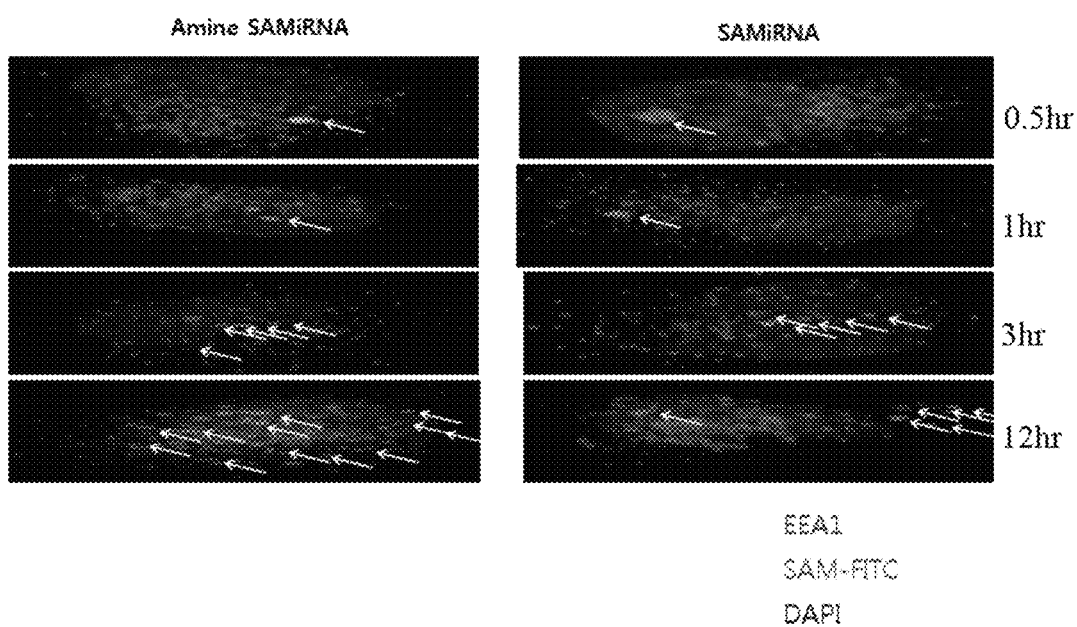

FIG. 18 shows confocal microscope images, at 0 hr., 0.5 hr., 1 hr., 3 hrs., and 12 hrs., for cell samples treated with amine SAMiRNA and SAMiRNA, conjugated with FITC fluorophore, with primary antibody staining (EEA1) of intracellular endosomes, secondary antibody red fluorescence staining (Alexa546), and nuclear staining (DAPI).

Figure 19:
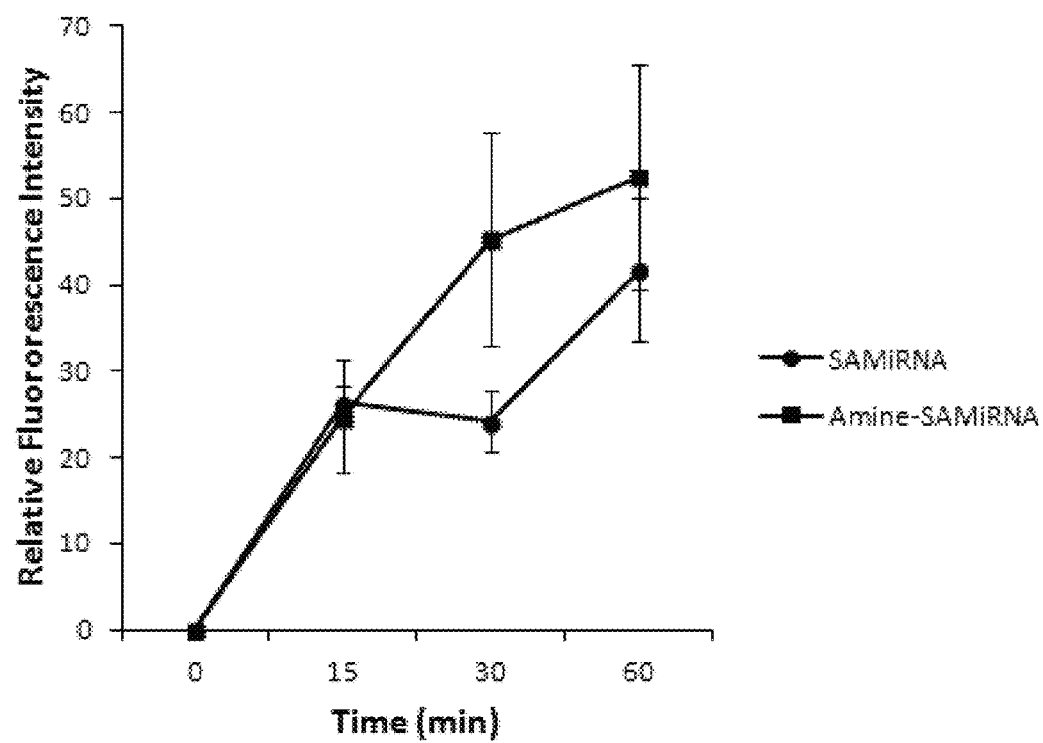

FIG. 19 is a graph of relative fluorescence intensity as a function of time, for SAMiRNA and amine-SAMiRNA, showing the effect of the amine group on intracellular delivery.

BEST MODE FOR CARRYING OUT THE INVENTION

Hereinafter, the present invention will be described in further detail with reference to examples. It will be obvious to a person having ordinary skill in the art that these examples are illustrative purposes only and are not to be construed to limit or change the scope of the present invention.

Example 1: Design of Target Nucleotide Sequence of Dengue Virus and Preparation of siRNA Dengue virus serotype 4 (bank accession No. KBPV-VR-31) obtained from the Korea Bank for Pathogenic Viruses (Korea) was transfected into VeroE6 cells, and after 4 days, cell pellets were harvested. RNA was prepared using a Qiagen RNA prep kit and quantified, and then cDNA was synthesized from 2 μg of the total RNA using an AccuPower Rocketscript™ RT Premix (Bioneer, Korea). The obtained cDNA was sequenced, and as a result, it was found that the sequence of the cDNA was consistent with the total nucleotide sequence of the dengue virus serotype 4 strain H241 (GenBank: AY947539.1), except for 11 nucleotides and 6 amino acids.

Based on such sequencing results, highly scored siRNAs and additional siRNAs selected so as to be uniformly distributed in functional proteins were combined using the siRNA design algorithms of the following four bio companies on the H241 nucleotide sequence, thereby designing a total of 50 siRNAs as shown in Table 2 below.

Bioneer: http://10.10.10.46:8080/siRNA2/menuDesigner.jsf;
Invitrogen: https://rnaidesigner.invitrogen.com/rnaiexpress;
Genscript: https://www.genscript.com/ssl-bin/gs_login;
ThermoScientific: http://www.thermoscientificbio.com/design-cented-redirect=true)

Figure 1:
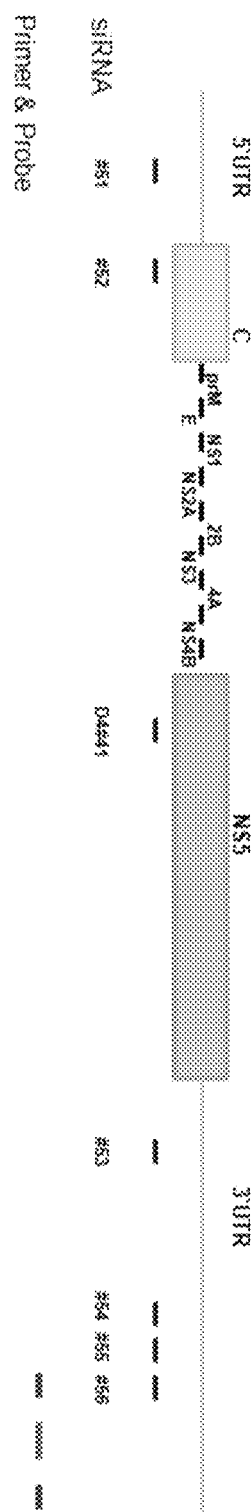
FIG. 1 shows the relative positions of universal siRNAs on the virus genome.

Next, the sequences of the 5'-UTR region and 3'-UTR region of the genome sequences of about 60 dengue virus strains belonging to four serotypes were multialigned to compare the homology, thereby obtaining a conserved sequence region having high homology. Thus, 6 universal siRNAs targeting the region were additionally constructed as shown in Table 3 below. The relative positions of these siRNAs are shown in FIG. 1.

TABLE 2

Sense strand sequences of 50 siRNAs selected using the genome of dengue virus serotype 4

| Seq. Position | Code Name | Sequence (sense strand of siRNA) | Protein | SEQ ID No. |
|---|---|---|---|---|
| 91 | SiRNA#1 | AGCAGATCTCTGGAAAAATGAAC | Cp | 1 |
| 347 | SiRNA#2 | GACTGGATTCAGGAAGGAGATAG | Cp | 2 |
| 362 | SiRNA#3 | AAGGAGATAGGCCGCATGCTG | Cp | 3 |
| 444 | SiRNA#4 | GCGTTTCACTTGTCAACAA | M | 4 |
| 893 | SiRNA#5 | CCAGCGAACAGTCTTCTTT | M | 5 |
| 965 | SiRNA#6 | GAACAGAGACTTTGTGGAA | Env | 6 |
| 1221 | SiRNA#7 | CGGAGAGATGTGGTAGACAGAGG | Env | 7 |
| 1331 | SiRNA#8 | GGTCCAAATTGAGAACCTT | Env | 8 |
| 1636 | SiRNA#9 | GGAATTACAAAGAGAGAAT | Env | 9 |
| 1679 | SiRNA#10 | CAAGAGACAGGATGTGACAGTGC | Env | 10 |

TABLE 2 -continued

Sense strand sequences of 50 siRNAs selected using the genome of dengue virus serotype 4

| Seq. Position | Code Name | Sequence (sense strand of siRNA) | Protein | SEQ ID No. |
|---|---|---|---|---|
| 1752 | SiRNA#11 | AAGTGGATTCCGGTGATGGAA | Env | 11 |
| 1803 | SiRNA#12 | AAGTTCGCATGGAGAAATTGA | Env | 12 |
| 1850 | SiRNA#13 | CTCAGGAAAGTTCTCAATTGACA | Env | 13 |
| 1957 | SiRNA#14 | AGATAAGAGATGTGAACAA | Env | 14 |
| 2117 | SiRNA#15 | GTTCAGGAAAGGGAGTTCCATTG | Env | 15 |
| 2512 | SiRNA#16 | GGACAGAACAGTACAAATT | NS1 | 16 |
| 2535 | SiRNA#17 | CCAGAGTCTCCAGCGAGACTAGC | NS1 | 17 |
| 2910 | SiRNA#18 | GGCATGTTTACGACCAACATATG | NS1 | 18 |
| 3072 | SiRNA#19 | AAGCATCTCTCATTGAAGTGA | NS1 | 19 |
| 3228 | SiRNA#20 | CCATGGCACTTGGGCAAAT | NS1 | 20 |
| 3248 | SiRNA#21 | GGAGATAGACTTTGGAGAA | NS1 | 21 |
| 3424 | SiRNA#22 | GGATGGAAATTAGGCCCTT | NS1 | 22 |
| 3543 | SiRNA#23 | GAAGAATGCTTGAGGAGAA | NS2A | 23 |
| 2981 | SiRNA#24 | ACCATAATGGCTGTGTTGTTTGT | NS2A | 24 |
| 4097 | SiRNA#25 | GCCAGTGTACCTAATGACTCTCA | NS2A | 25 |
| 4121 | SiRNA#26 | GAAAGGAGCTTCAAAGAGA | NS2B | 26 |
| 4159 | SiRNA#27 | GTATAATGGCTGTGGGTTT | NS2B | 27 |
| 4809 | SiRNA#28 | AAGATGTTCAGGTTCTAGCTA | NS3 | 28 |
| 4927 | SiRNA#29 | GAACATCTGGTTCTCCCATCATT | NS3 | 29 |
| 4970 | SiRNA#30 | CGGACTCTACGGAAATGGAGTAG | NS3 | 30 |
| 5524 | SiRNA#31 | TAGAAGACATCGAGAGAGA | NS3 | 31 |
| 5547 | SiRNA#32 | CCAGAAAGGTCATGGAACA | NS3 | 32 |
| 5574 | SiRNA#33 | GACTGGATAACCGACTACCAAGG | NS3 | 33 |
| 6250 | SiRNA#34 | AAGAAAACATGGAGGTTGAAATT | NS3 | 34 |
| 6605 | SiRNA#35 | AGGAAAAGGAATAGGGAAA | NS4A | 35 |
| 6774 | SiRNA#36 | AAGACAATCAATTGATCTACG | NS4A | 36 |
| 7136 | SiRNA#37 | AACGACCTTGATAGCATCCTTAG | NS4B | 37 |
| 7277 | SiRNA#38 | AGTAATAGATCTAGAACCA | NS4B | 38 |
| 7608 | SiRNA#39 | AAGAGACAGCTAAACTCACTAGA | NS5 | 39 |
| 7649 | SiRNA#40 | GTACAAAAGAAGTGGAATA | NS5 | 40 |
| 7778 | SiRNA#41 | GGTAAAACCAAAAGGGAAA | NS5 | 41 |
| 8043 | SiRNA#42 | GGAAGAACATTAAGAGTTT | NS5 | 42 |
| 8149 | SiRNA#43 | TGGAGAAACTGCAGAGAAA | NS5 | 43 |
| 8452 | SiRNA#44 | ATCAGGAAAACCCATACAGAACC | NS5 | 44 |
| 9477 | SiRNA#45 | CCAAAAGGGTTGAAAGAAA | NS5 | 45 |
| 9804 | SiRNA#46 | GGATGGAGTTTAAGAGAAA | NS5 | 46 |
| 10055 | SiRNA#47 | TCCAGTTCATTCGTGGGAAGACA | NS5 | 47 |

TABLE 2 -continued

Sense strand sequences of 50 siRNAs selected using the genome of dengue virus serotype 4

| Seq. Position | Code Name | Sequence (sense strand of siRNA) | Protein | SEQ ID No. |
|---|---|---|---|---|
| 10428 | SiRNA#48 | GGCATATTGGACTAGCGGTTAGA | 3'UTR | 48 |
| 10567 | SiRNA#49 | GCATATTGACGCTGGGAAA | 3'UTR | 49 |
| 10587 | SiRNA#50 | ACCAGAGATCCTGCTGTCTCTGC | 3'UTR | 50 |

TABLE 3

Sense strand sequences of universal siRNAs selected from region showing high homology

| Seq. Position | Code Name | Sequence (sense strand of siRNA) | Protein | SEQ ID No. |
|---|---|---|---|---|
| 87 | SiRNA#51 | AGAGAGCAGAUCUCUGGAAAA | 5'UTR | 51 |
| 142 | SiRNA#52 | UCAAUAUGCUGAAACGCGAGA | CP | 52 |
| 10444 | SiRNA#53 | GGUUAGAGGAGACCCCUCCCA | 3'UTR | 53 |
| 10528 | SiRNA#54 | GGACUAGAGGUUAGAGGAGAC | 3'UTR | 54 |
| 10562 | SiRNA#55 | AAACAGCAUAUUGACGCUGGG | 3'UTR | 55 |
| 10586 | SiRNA#56 | GACCAGAGAUCCUGCUGUCUC | 3'UTR | 56 |

In addition, siCONT (having a sense strand of SEQ ID NO: 89), which is a siRNA that does not inhibit the expression of any gene, was prepared (Table 4). The siRNA was prepared by connecting the phosphodiester bonds of the RNA backbone structure using (3-cyanoethyl phosphoramidite (Nucleic Acids Research, 12:4539-4557, 1984). Specifically, a series of processes including deblocking, coupling, oxidation and capping were repeated on a nucleotide-bound solid support using a RNA synthesizer (384 Synthesizer, BIONEER, KOREA), thereby obtaining a reaction product comprising a RNA having a desired length. The RNA was separated and purified from the reaction product by HPLC LC918 (Japan Analytical Industry, Japan) equipped with a Daisogel C18 column (Daiso, Japan), and was analyzed by a MALDI-TOF mass spectrometer (Shimadzu, Japan) to confirm whether it was consistent with the desired nucleotide sequence. Next, the sense and antisense RNA strands were bound to each other, thereby preparing a double-stranded siRNA comprising a sense strand having a sequence selected from among the sequences of SEQ ID NOS: 1 to 56 and 89.

TABLE 4

Sense strand sequence of negative control siCONT siRNA that does not inhibit expression of any gene

| Code Name | Sequence (sense strand of siRNA) | SEQ ID No. |
|---|---|---|
| siCONT | CUUACGCUGAGUACUUCGA | 89 |

Example 2: Culture and Replication of Dengue Virus Serotypes 2, 3 and 4

2.1: Infection and Culture of Cells

A 12-well plate was seeded with C6/36 cells ($2.5 \times 10^5$/well) and Vero E6 cells ($1 \times 10^5$/well), and washed with DPBS immediately before infection with dengue virus.

After dengue virus infection, the viral culture was collected at 24-hr intervals and centrifuged (6000 rpm, 5 min, 4° C.). From 400 μl of the culture, RNA was prepared using an ExiPrep™ 16DX RNA prep system. Of a total of 50 μl of the eluted RNA, 19.5 μl was used for cDNA synthesis, and of a total of 20 μl of the cDNA, 5 μl was used for qPCR.

Among the dengue virus serotypes used, serotype 2 to serotype 4 were obtained from the Korea Bank for Pathogenic Viruses (Korea), and serotype 1 was obtained from the Department of Virology, the Korea Centers for Disease Control and Prevention.

2.2: Examination of Viral Copy Number

From a total of 400 μl of the collected culture media, RNA was extracted using Exiprep Dx™ (Bioneer, Korea) system. Using this system, about 50 μl of RNA per 400 μl of the culture media was obtained.

Then, 0.5 μl of an antisense primer (100 pM/μl) having the primer sequence shown in Table 5 below and 19.5 μl of the prepared RNA were reacted using AccuPower® CycleScript RT PreMix (Bioneer, Korea) at 50° C. for 1 hr and at 95° C. for 5 min, thereby obtaining a total of 20 μl of a cDNA sample for each virus serotype. Then, for qPCR, the detection of serotypes 1 to 3 was performed using DN1234_S, DN123_AS and DN123_probe, and the detection of serotype 4 was performed using DN1234_S, DN4_AS and DN4_probe.

In the qPCR reaction, AccuPower® Plus DualStar™ qPCR PreMix (Bioneer, Korea) was used, and 0.3 μl (based on 100 pM/μl stock) of each of the primer and the probe, 5 μl of cDNA and 44.1 μl of dH$_2$O were added to a total of 50 μl of a reaction volume and mixed by vortexing for about 3-5 minutes. The reaction was performed using Exicycler™ 96 Real-Time Quantitative Thermal Block (Bioneer, Korea) at 95° C. for 10 min and for 45 cycles (95° C. for 5 sec, and 60° C. for 5 sec, and the fluorescence value was detected after each cycle. Based on the results obtained after the qPCR array, the viral copy number of each sample and the relative amount (%) of residual virus were calculated.

TABLE 5

Primer sequences used in experiment

| DN1234_S | CTGGGAGAGACCAGAGATCC |
|---|---|
| DN123_AS | GTTGATTCAACAGCACCATTCC |

TABLE 5 -continued

Primer sequences used in experiment

| | |
|---|---|
| DN123_probe | 5FAM-CATCATTCCAGGCACAGAACGCCA-3BHQ1 |
| DN1234_S | CTGGGAGAGACCAGAGATCC |
| DN4_AS | GTTGGATCAACAACACCAATCC |
| DN4_probe | 5FAM-CATCAATCCAGGCACAGAGCGCCG-3BHQ1 |

2.3: Replication Kinetics of Virus

Figure 2:
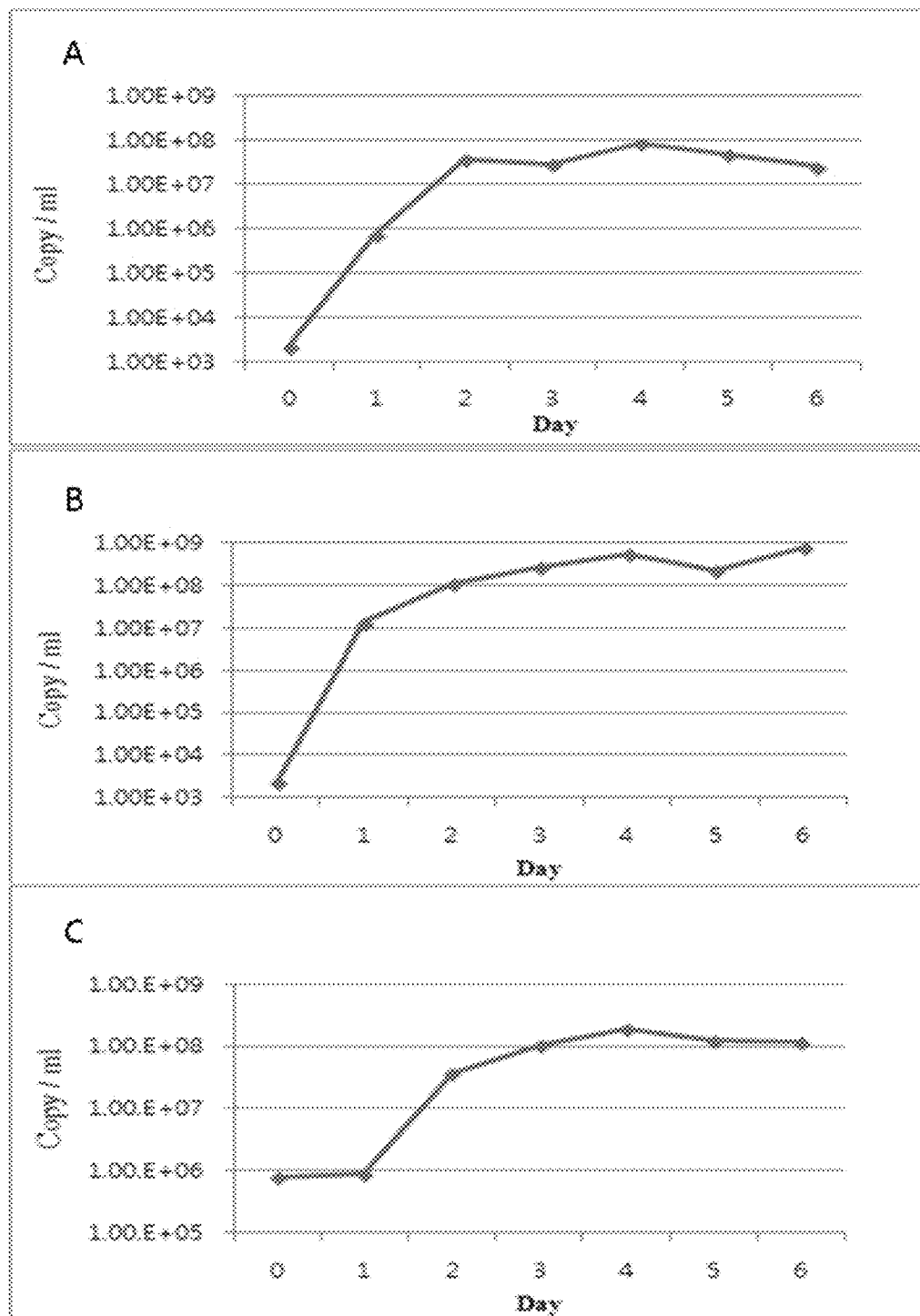
FIG. 2 is a set of graphs showing the replication kinetics of each serotype of dengue virus in a C6/36 cell line.

On each day, two samples are analyzed in duplicate, and the four values were averaged. Based on the averaged values, the qPCR results were graphically shown. As a result, the copy numbers of serotypes 2, 3 and 4 in the C6/36 cell line increased rapidly up to 72 hours after infection, and then were maintained (FIG. 2). In the case of the VeroE6 cell line, it was observed that the copy numbers of serotypes 2 and 3 increased rapidly up to 72 hours after infection, and then were maintained, and the copy number of serotype 4 gradually increased up to 144 hours (FIG. 3). Thus, for virus replication, the virus was collected at 7 days after infection, and for evaluation of siRNA efficacy, the culture medium was collected at day 3 when the virus replication reached the peak point. Although the results of quantitative measurement of the copy number of serotype 1 were not described in the specification, serotype 1 was used in the Examples under the same conditions according to the same method as other serotypes.

Example 3: Examination of the Ability of Primarily Selected siRNAs to Inhibit Dengue Virus Replication 3.1: siRNA Transfection and Virus Infection VeroE6 cells were transfected with 56 kinds of siRNAs constructed in Example 1, and the copy number of virus in the transfected cell line was analyzed to determine the performance of the siRNAs.

24 hours before siRNA transfection, VeroE6 cells were seeded into a 12-well plate (Nunc, USA) at a density of $1 \times 10^5$ cells/well. The cells were cultured using 1 ml/well of a complete medium of DMEM (Hyclone, USA) under the conditions of 37° C. and 5% $CO_2$. The complete medium composition was obtained by adding 4.00 mM of L-glutamine and 4500 mg/L of glucose, sodium pyruvate and fetal bovine serum (Hyclone, USA) to 500 ml of Dulbeccos Modified Eagles Medium (pH 7.4) to a final concentration of 10%. After 24 hours, for siRNA transfection, the medium in the 12-well plate was replaced with 500 µl of OPTI-MEM (GIBCO, USA), and the cells were pre-incubated in a 5% $CO_2$ incubator at 37° C. Each of a mixture of 3.5 µl of LipofectamineRNAimax (Invitrogen, USA) reagent and 250 µl of OPTI-MEM and 250 µl of OPTI-MEM containing at various concentrations of the siRNA diluted therein was prepared, and then allowed to stand at room temperature for 5 minutes, after which the OPTI-MEM containing the siRNA diluted therein was added to the LipofectamineR-NAimax-containing OPTI-MEM and incubated at room temperature for about 20 minutes. The incubated medium was transfected into cells. After about 6 hours, the medium was washed out and exchanged with complete DMEM medium containing 10% FBS, and the cells were incubated in a 5% $CO_2$ incubator at 37° C. for 24 hours. After 24 hours, the medium was washed out, and then the prepared virus soup (about $1.0 \times 10^8$ copies/ml) was 2-fold diluted and controlled to more than $1 \times 10^7$ copies per 200 µl. 200 µl of the dilution was added to each well, and then rocked at 30-min intervals for 2 hours to promote the application of the virus, and then 1 ml of 2% FBS-containing DMEM medium (virus growth medium) was added thereto and incubated before an assay was performed. After about 3 days, RNA was extracted from the harvested cell culture medium and the virus copy number was measured.

3.2: Examination of the Ability of 56 siRNAs to Inhibit Dengue Virus Serotype 4

To select candidates having the ability to inhibit the replication of virus serotype 4 from a total of 56 designed siRNA candidates (Tables 2 and 3), treatment with 20 nM of the siRNA was performed, followed by a screening experiment. In each experiment, the residual virus value of the siRNA siCONT control group was set at 100%, the residual virus values of the siRNA candidates were expressed as value relative thereto for comparison. As a result, as can be seen in FIG. 4, 30 or more siRNAs showed a residual virus value of less than 15%, suggesting that these have a high ability to inhibit dengue virus.

Accordingly, 23 siRNA candidates (SiRNA#4, SiRNA#5, SiRNA#6, SiRNA#7, SiRNA#8, SiRNA#13, SiRNA#16, SiRNA#20, SiRNA#22, SiRNA#23, SiRNA#29, SiRNA#32, SiRNA#34, SiRNA#39, SiRNA#40, SiRNA#41, SiRNA#42, SiRNA#44, SiRNA#45, SiRNA#46, SiRNA#47, SiRNA#51, and SiRNA#52) showing a high ability to inhibit dengue virus at a concentration of 20 nM were primarily selected.

The primarily selected siRNA candidates were siRNAs having sense strands having the sequences of SEQ ID NOS: 4 to 8, 13, 16, 20, 22, 23, 29, 32, 34, 39 to 42, 44 to 47, 51 and 52, respectively (Tables 2 and 3).

In the present invention, siRNA of "SiRNA#X" means a siRNA comprising a sense strand having a sequence represented by SiRNA#X in Tables 2, 3 and 6.

3.3: Analysis of the Ability of Primarily Selected Five siRNA Candidates to Inhibit Dengue Virus Serotype 4

In order to verify whether the 23 siRNA candidates selected in Example 3.2 above have an inhibitory effect on the replication of dengue virus serotype 4, a screening experiment by treatment with 5 nM of the siRNA was performed, thereby selecting five siRNA candidates (SiRNA#4, SiRNA#16, SiRNA#22, SiRNA#51, and SiRNA#52).

Then, in order to confirm whether the selected five siRNAs have an inhibitory effect on the replication of all dengue virus serotypes, the inhibitory effect on the replication of dengue virus serotype 4 was examined by treatment with 10 nM of the siRNA. Herein, siRNA (UnisiRNA-sh) having the same sequence as that of shRNA described in Korrapati A B et al., *PLoS Negl Trop Dis.* 6(7):e1735, 2012 was used as a positive control.

As a result, it was shown that the selected five siRNA candidates (SiRNA#4, SiRNA#16, SiRNA#22, SiRNA#51, and SiRNA#52) had excellent dengue virus replication inhibitory ability compared to UnisiRNA-sh (FIG. 5).

In addition, in order to examine whether the finally selected five siRNA candidates (SiRNA#4, SiRNA#16, SiRNA#22, SiRNA#51, and SiRNA#52) have a dose-dependent effect on the inhibition of replication of dengue virus serotype 4, a screening experiment was performed at four concentrations of 20 nM, 10 nM, 5 nM and 1 nM.

As a result, the five siRNA candidates mostly showed a residual virus value of about 10% at a concentration of 5 nM or more, particularly 10 nM or more, suggesting that these have virus inhibitory ability. However, it could be seen that, when the concentration was reduced to 1 nM, the inhibitory ability decreased. Through this experiment, it could be seen that the five siRNAs all showed high inhibitory ability when they were used at a concentration of 10 nM or higher (FIG. 6).

3.4: Analysis of Inhibitory Effects of Primarily Selected Five siRNAs on Each Dengue Virus Serotype In order to examine whether the primarily selected five siRNA candidates show inhibitory ability against each dengue virus serotype, each screening experiment was performed using four dengue virus serotypes.

As a result, it was shown that when the experiment was performed at a siRNA concentration of 10 nM, SiRNA#51 and SiRNA#52 showed high inhibitory ability against most of the serotypes, and the remaining three siRNAs showed insignificant inhibitory ability against the serotypes except for serotype 4 (FIG. 7).

Examples 4: Preparation of Secondary Universal siRNAs by Single Nucleotide Sliding Window Scanning 4.1: Design and Preparation of Secondary siRNAs
Based on the sequence of each of SiRNA#51 및 SiRNA#52 constructed to target a conserved sequence region having high homology to the 5'-UTR region and Cp region of the dengue virus genome, 16 new universal siRNAs (a total of 32 siRNAs) as shown in Table 6 were additionally constructed by a single nucleotide sliding window scanning design method. FIG. 8 shows the relative positions of these siRNAs.

TABLE 6

Sense strand sequences of secondary universal siRNAs designed by single nucleotide sliding window scanning from universal SiRNA#51 and SiRNA#52 selected from region showing high homology

| Code Name | Sequence (sense strand of siRNA) | SEQ ID No. |
|---|---|---|
| SiRNA#51-1 | AAUUAGAGAGCAGAUCUCU | 57 |
| SiRNA#51-2 | AUUAGAGAGCAGAUCUCUG | 58 |
| SiRNA#51-3 | UUAGAGAGCAGAUCUCUGG | 59 |
| SiRNA#51-4 | UAGAGAGCAGAUCUCUGGA | 60 |
| SiRNA#51-5 | AGAGAGCAGAUCUCUGGAA | 61 |
| SiRNA#51-6 | GAGAGCAGAUCUCUGGAAA | 62 |
| SiRNA#51-7 | AGAGCAGAUCUCUGGAAAA | 63 |
| SiRNA#51-8 | GAGCAGAUCUCUGGAAAAA | 64 |
| SiRNA#51-9 | AGCAGAUCUCUGGAAAAAU | 65 |
| SiRNA#51-10 | GCAGAUCUCUGGAAAAAUG | 66 |
| SiRNA#51-11 | CAGAUCUCUGGAAAAAUGA | 67 |
| SiRNA#51-12 | AGAUCUCUGGAAAAAUGAA | 68 |
| SiRNA#51-13 | AGAGAGCAGAUCUCUGAUG | 69 |
| SiRNA#51-14 | GAGAGCAGAUCUCUGAUGA | 70 |
| SiRNA#51-15 | AGAGCAGAUCUCUGAUGAA | 71 |
| SiRNA#51-16 | GAGCAGAUCUCUGAUGAAU | 72 |

TABLE 6 -continued

Sense strand sequences of secondary universal siRNAs designed by single nucleotide sliding window scanning from universal SiRNA#51 and SiRNA#52 selected from region showing high homology

| Code Name | Sequence (sense strand of siRNA) | SEQ ID No. |
|---|---|---|
| SiRNA#52-1 | CUUUCAAUAUGCUGAAACG | 73 |
| SiRNA#52-2 | UUUCAAUAUGCUGAAACGC | 74 |
| SiRNA#52-3 | UUCAAUAUGCUGAAACGCG | 75 |
| SiRNA#52-4 | UCAAUAUGCUGAAACGCGA | 76 |
| SiRNA#52-5 | CAAUAUGCUGAAACGCGAG | 77 |
| SiRNA#52-6 | AAUAUGCUGAAACGCGAGA | 78 |
| SiRNA#52-7 | AUAUGCUGAAACGCGAGAG | 79 |
| SiRNA#52-8 | UAUGCUGAAACGCGAGAGA | 80 |
| SiRNA#52-9 | AUGCUGAAACGCGAGAGAA | 81 |
| SiRNA#52-10 | UGCUGAAACGCGAGAGAAA | 82 |
| SiRNA#52-11 | GCUGAAACGCGAGAGAAAC | 83 |
| SiRNA#52-12 | CUGAAACGCGAGAGAAACC | 84 |
| SiRNA#52-13 | UGAAACGCGAGAGAAACCG | 85 |
| SiRNA#52-14 | GAAACGCGAGAGAAACCGC | 86 |
| SiRNA#52-15 | AAACGCGAGAGAAACCGCG | 87 |
| SiRNA#52-16 | AACGCGAGAGAAACCGCGU | 88 |

4.2: Examination of the Ability of Secondarily Selected 32 siRNAs to Inhibit Dengue Virus Serotypes 2 and 3

In order to select highly efficient universal siRNAs because the inhibitory ability of the primarily selected SiRNA#51 and SiRNA#52 appeared when most serotypes were treated with 10 nM of the siRNAs, a screening experiment of comparing the inhibitory ability against serotypes 2 and 3 with the primary 32 siRNAs at a concentration of 10 nM was performed using the sequences of SiRNA#51 and SiRNA#52 newly designed by the single nucleotide sliding window scanning method.

As a result, the experiment group treated with siRNAs of SiRNA#51-14 (SEQ ID NO: 70), SiRNA#51-15 (SEQ ID NO: 71), SiRNA#51-16 (SEQ ID NO: 72), SiRNA#52-4 (SEQ ID NO: 76), SiRNA#52-5 (SEQ ID NO: 77), SiRNA#52-8 (SEQ ID NO: 80), SiRNA#52-9 (SEQ ID NO: 81) and SiRNA#52-10 (SEQ ID NO: 82) showed a residual virus value of less than 1%, suggesting that these siRNAs show a very strong inhibitory ability. This value is a significantly better inhibitory ability value compared to those of previous SiRNA#51 and SiRNA#52.

4.3: Examination of the Ability of Finally Selected Two siRNAs to Inhibit Replication of Dengue Virus Serotypes 2 to 4

Next, among the siRNAs constructed based on the sequences of SiRNA#51 and SiRNA#52 among the siRNA candidates showing strong inhibitory ability, SiRNA#51-15 (SEQ ID NO: 71) and SiRNA#52-10 (SEQ ID NO: 82) having high reproducibility were finally selected, and the inhibitory effects thereof against the replication of dengue virus serotypes 2 to 4 were examined at a concentration of 10 nM.

Figure 10A:
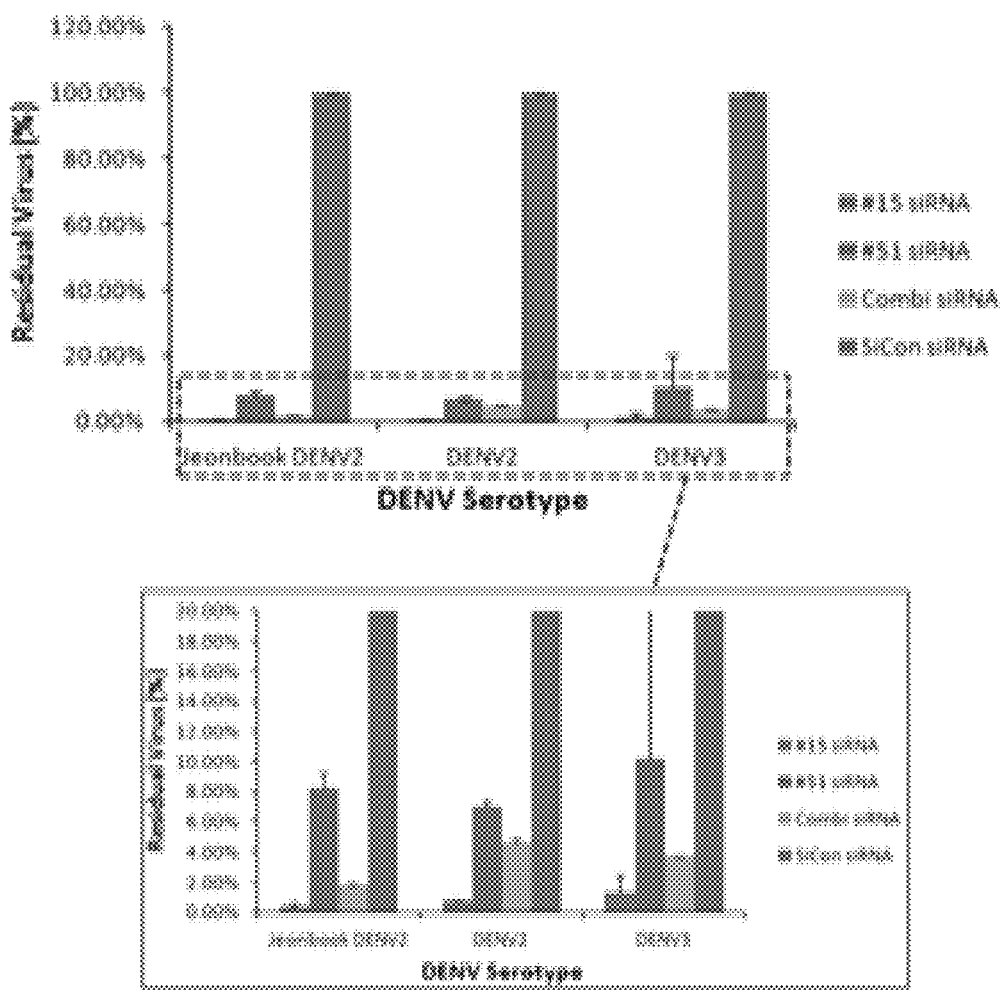
Figure 10B:
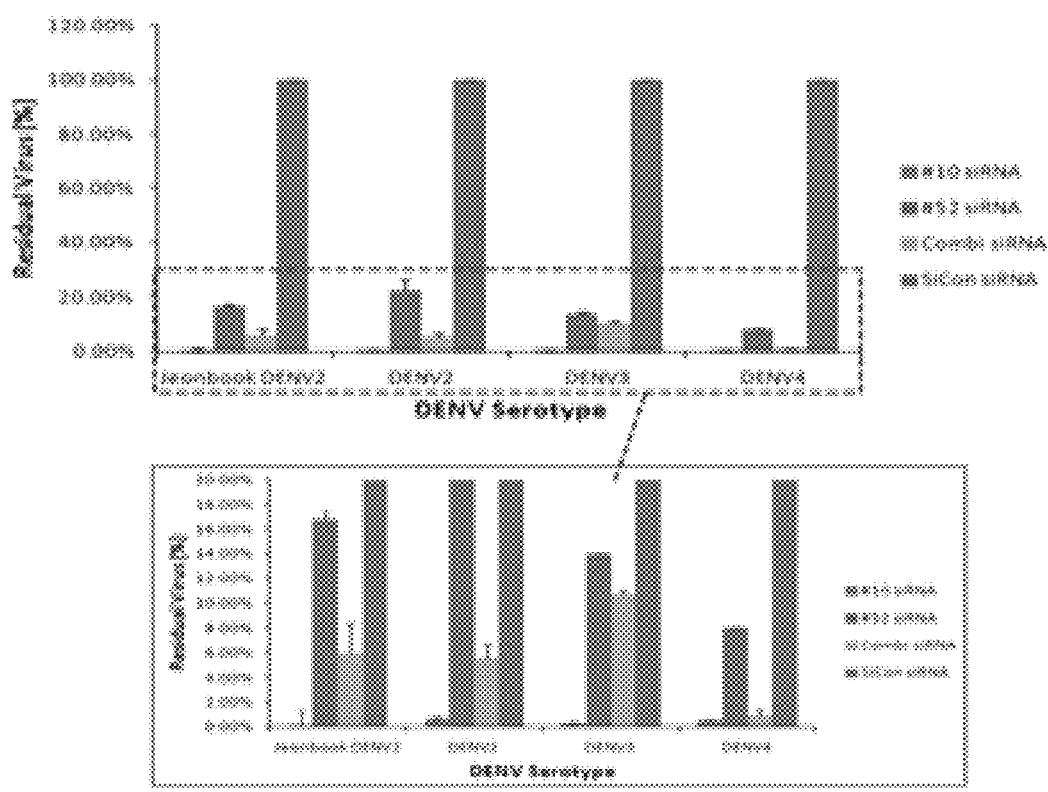

As a result, it could be seen that SiRNA#51-15 and SiRNA#52-10 showed high inhibitory effects compared to previous SiRNA#51 and SiRNA#52 (FIGS. 10A-10B).

4.4: Examination of the Effect of Combination of SiRNA#51-15 and SiRNA#52-10 Against the Replication of Dengue Virus Serotypes 2 to 4

As described above, the two siRNAs (SiRNA#51-15 and SiRNA#52-10) having better inhibitory ability against the replication of dengue virus serotypes 2, 3 and 4 were selected through the single nucleotide sliding windows scanning experiment. However, based on the fact that a single siRNA cannot be sufficient for use as a universal therapeutic agent for inhibiting the replication of al dengue virus serotypes (SiRNA#51-15 does not show strong inhibitory ability against dengue virus serotype 4), SiRNA#51-15 and SiRNA#52-10 were mixed at a molar ratio of 1:1 to prepare a siRNA mixture (hereinafter referred to as 'Combi-siRNA'), and a screening experiment was performed at a concentration of 10 nM in order to confirm whether Combi-siRNA can show a strong inhibitory effect by a complementary effect against the replication of all dengue virus serotypes.

As a result, it could be seen that Combi-siRNA showed a strong inhibitory effect against the replication of all dengue virus serotypes (FIG. 11).

4.5: Examination of Inhibitory Effect of Combination of SiRNA#51-15 and SiRNA#52-10 Against the Replication of Dengue Virus Serotypes 2 to 4 in a Pre-Virus Infection Condition Established to Make a Therapeutic Agent Application Environment Caused by Infection in Nature Next, cells cultured in view of a virus infection state caused by mosquitoes were infected with the virus, and then treated with the siRNA, and whether the siRNA can exhibit a therapeutic effect was examined.

Specifically, 5 nM of each of the selected two siRNAs (SiRNA#51-15 and SiRNA#52-10) was added, and 5 nM of siCONT was added thereto to control the final concentration of the siRNA to 10 nM. Also, the cells were treated with Combi-siRNA containing 5 nM of each of the two siRNAs (SiRNA#51-15 and SiRNA#52-10), and the inhibitory ability of Combi-siRNA was examined. As a result, it was shown that treatment with Combi-siRNA showed strong inhibitory ability against the replication of all dengue virus serotypes (FIG. 12).

This suggests that Combi-siRNA can function as a universal therapeutic agent against all dengue virus serotypes.

4.6: Determination of Inhibitory Effect and $IC_{50}$ Value of Combi-siRNA Against Replication of all Dengue Virus Serotypes In order to verify whether the finally selected two siRNAs (SiRNA#51-15 and SiRNA#52-10) and Combi-siRNA have a dose-dependent inhibitory effect on the replication of dengue virus JB (serotype 2, Chonbuk National University) and dengue virus serotypes 1 to 4, a screening experiment was performed at four concentrations of 10 nM, 1 nM, 200 pM and 50 pM.

As a result, the siRNA candidates showed different dose-dependent inhibitory effects against all dengue virus serotypes (FIG. 13), and showed an $IC_{50}$ value at a low concentration of 50-200 pM for most virus serotypes except for dengue virus serotype 4. Combi-siRNA showed a better $IC_{50}$ value compared to the siRNAs (Table 7).

TABLE 7

$IC_{50}$ values of finally selected two siRNAs (SiRNA#51-15 and SiRNA#52-10) and Combi-siRNA against the replication of all dengue virus serotypes (serotypes 1 to 4 and JB2)

| | $IC_{50}$ values of each DENV serotype (nM) | | | | |
|---|---|---|---|---|---|
| Serotypes | DENV1 | DENV2 | DENV JB2 | DENV3 | DENV4 |
| SiRNA#51-15 | <0.05 | <0.2 | <0.05 | <0.2 | <10.0 |
| SiRNA#52-10 | <0.2 | <0.2 | <0.2 | <0.2 | <1.0 |
| Combi-siRNA | <0.05 | <0.2 | <0..05 | <0.2 | <1.0 |

Example 5: Examination of the Ability of SAMiRNA Nanoparticles to Inhibit Dengue Virus Replication 5.1: Preparation of Double-Stranded Oligo RNA Structure (SAMiRNA)

The double-stranded oligo RNA structure (SAMiRNA) prepared in the present invention has a structure as shown in the following structural formula (16):

Structural formula (16)

wherein S represents a siRNA sense strand, AS represents a siRNA antisense strand, PEG represents polyethylene glycol that is a hydrophilic compound, $C_{24}$ represents a disulfide bond-containing tetradocosane that is a hydrophobic compound, and 5' and 3' represents the direction of the ends of the double-stranded oligo RNA.

The siRNA sense strand in structural formula (16) above was prepared by synthesizing a double stranded oligo RNA-hydrophilic compound structure having polyethylene glycol bound to the 3' end region by a method in which the phosphodiester bonds of the RNA backbone structure were connected by β-cyanoethyl phosphoramidite using a 3' polyethylene glycol (PEG, Mn=2,000)-CPG support prepared according to the method described in Example 1 of Korean Patent Publication No. 2012-0119212, and then binding a disulfide bond-containing tetradocosane to the 5' end, thereby preparing a desired RNA-polymer sense strand. The antisense strand to be annealed to the above sense strand was obtained by preparing an antisense strand having a sequence complementary to that of the sense strand using the above-described reaction.

After completion of the synthesis, the synthesized RNA single strand and RNA polymer structure were detached from the CPG by treatment with 28% (v/v) ammonia in water bath at 60° C., followed by deprotection to remove the protecting group. The deprotected RNA single strand and RNA-polymer structure were treated with a mixture of N-methylpyrolidon, triethylamine and triethylaminetrihydrofluoride at a volume ratio of 10:3:4 in an oven at 70° C. to remove 2'TBDMS (tert-butµldimethylsilyl).

RNA was separated and purified from the reaction product by HPLC LC918 (Japan Analytical Industry, Japan) equipped with a Daisogel C18 column (Daiso, Japan), and analyzed by a MALDI-TOF mass spectrometer (Shimadzu, Japan) to confirm whether it is consistent with the desired nucleotide sequence. Then, in order to prepare each double-stranded oligo RNA polymer structure, the sense strand was mixed with the same amount of the antisense strand, and the mixture was added to 1× annealing buffer (30 mM HEPES, 100 mM potassium acetate, 2 mM magnesium acetate, pH 7.0-7.5), and allowed to react in water bath at 90° C. for 3 minutes, and then allowed to react at 37° C., thereby preparing double-stranded oligo RNA structures comprising the finally selected five siRNA candidates (SiRNA#4, SiRNA#16, SiRNA#22, SiRNA#51, and SiRNA#52), respectively. It was confirmed by electrophoresis that the prepared double-stranded oligo RNA structures were annealed.

The prepared double-stranded oligo RNA structure (SAMiRNA) forms nanoparticles (i.e., micelles) by interactions between the hydrophobic compound moieties bound to the ends of the double-stranded oligo RNAs (FIG. 14). The prepared SAMiRNA was dissolved in 1.5 ml of DPBS (Dμlbecco's Phosphate Buffered Saline) at a concentration of 50 μg/ml, and then lyophilized at −75° C. and 5 mTorr for 48 hours to prepare nanoparticle powder, which was then dissolved in the solvent DPBS to prepare homogeneous nanoparticles, which were used in the Examples of the present invention.

5.2 Analysis of Virus Replication Inhibitory Ability of SAMiRNAs Comprising Primarily Selected Five siRNA Candidates Using the SAMiRNAs prepared by the method of Example 5.1 so as to include the primarily selected five siRNA candidates (SiRNA#4, SiRNA#16, SiRNA#22, SiRNA#51, and SiRNA#52), the inhibitory effects of the SAMiRNAs on the replication of dengue virus serotypes 3 and 4 were analyzed.

It was shown that when the SAMiRNAs comprising SiRNA#51 and SiRNA#52 showing high inhibitory ability against all dengue virus serotypes in the above Examples were used, they were delivered into cells at a concentration of about 200 nM or higher and showed high inhibitory ability (70-75%) (FIG. 15).

5.3 Analysis of Reproducibility of Universal Inhibitory Ability of Selected Finally Combi-siRNA Candidate in the Form of Mono-HEG-SAMiRNA Unlike the SAMiRNA used in Example 5.2, the hydrophilic compound block [$PO_3^-$ hexaethylene glycol]$_4$ was used in place of the hydrophilic compound PEG to prepare a highly stable SAMiRNA comprising both SiRNA#51-15 and SiRNA#52-10 (hereinafter referred to as 'Mono-HEG SAMiRNA'; see structural formula (17)).

$C_{24}$-5'-S-3'-[(Hexa Ethylene Glycol)-$PO_3^-$]$_4$    Structural formula (17)

wherein S represents the sense strand of the dengue virus-specific siRNA, AS represents the antisense strand of the dengue virus-specific siRNA, Hexa ethylene glycol represents a hydrophilic compound, $C_{24}$ represents a disulfide-containing tetradocosane that is a hydrophobic compound, and 5' and 3' represents the direction of the ends of the sense strand in the double-stranded oligo RNA.

In order to confirm whether the constructed Mono-HEG SAMiRNA reproducibly shows similar inhibitory abilities against all dengue virus serotypes, screening at a concentration of 500 nM was performed. As a result, it could be seen that treatment with Mono-HEG SAMiRNA reproducibly showed similar inhibitory abilities against all serotype (FIG. 16).

5.4: Analysis of Dose-Dependent Inhibitory Ability and Determination of $IC_{50}$ of Finally Selected Combi-siRNA Candidates in the Form of Mono-HEG-SAMiRNA Combi-siRNA obtained by mixing the finally selected two siRNAs (SiRNA#51-15 and SiRNA#52-10) at a molar ratio of 1:1 was synthesized in the form of SAMiRNA, and whether the SAMiRNA efficiently inhibits dengue virus replication to 50% even at low concentration in vitro, thereby evaluating the effectiveness of the SAMiRNA as an actual therapeutic agent.

Specifically, using Mono-HEG-SAMiRNA comprising both SiRNA#51-15 and SiRNA#52-10, a screening experiment of verifying the effect of inhibiting the replication of all dengue virus serotypes was performed at concentrations of 500 nM, 200 nM and 50 nM.

As a result, it could be seen that Mono-HEG-SAMiRNA showed reproducible $IC_{50}$ values against serotypes except for dengue virus serotype 4 at a concentration of 50-200 nM (FIG. 17 and Table 8).

TABLE 8

$IC_{50}$ value of SAMiRNA comprising Combi-siRNA against each dengue virus serotype

| | $IC_{50}$ values of each DENV serotype (nM) | | | | |
|---|---|---|---|---|---|
| Serotypes | DENV1 | DENV2 | DENV JB2 | DENV3 | DENV4 |
| Combi-siRNA | <50 | <200 | <200 | <200 | <200 |

Example 6: Comparative Analysis of the Intracellular Uptake and Endosomal Escape Efficiencies of SAMiRNA Carriers Obtained by Introducing Amine Group into SAMiRNA Nanoparticles In order to increase the intracellular delivery efficiency of Mono-HEG-SAMiRNA represented by structural formula (17) above, newly modified amine-Mono-HEG-SAMiRNA was synthesized by conjugating an amine group to the 3' end of the sense strand as shown in the following structural formula (18):

Structural formula (18)

$C_{24}$-5'-S-3'-[(Hexa Ethylene Glycol)-$PO_3^-$]$_4$—$C_6$—$NH_2$

AS wherein S represents the sense strand of the dengue virus-specific siRNA, AS represents the antisense strand of the dengue virus-specific siRNA, Hexa ethylene glycol represents a hydrophilic compound, $C_6$ represents a $C_6$ alkyl linker that connects an amine group to [Hexa Ethylene Glycol]$_4$, $C_{24}$ represents a disulfide-containing tetradocosane that is a hydrophobic compound, and 5' and 3' represents the direction of the ends of the sense strand in the double-stranded oligo RNA.

The newly synthesized amine-Mono-HEG-SAMiRNA was constructed by conjugating a FITC fluorophore to the 3' end region of the antisense strand such that an increase in the delivery efficiency thereof by the introduction of the amine group compared to the Mono-HEG-SAMiRNA could be visibly measured by a fluorescence microscope. In this experiment, the time-dependent delivery efficiencies of Mono-HEG-SAMiRNA and amine-Mono-HEG-SAMiRNA were randomly captured with the image data obtained a confocal microscope, and the fluorescence was quantitatively measured by a densitometer, thereby confirming whether the delivery efficiency of SAMiRNA was increased by the introduction of the amine group.

6.1: Comparison of Time-Dependent Delivery Efficiency of Mono-HEG-SAMiRNA-FITC by Comparative Observation of Fluorescence Images Using Confocal Microscope 15 hours before treatment with Mono-HEG-SAMiRNA-FITC, HeLa cells were seeded into a 2-chamber polystyrene vessel (BD Falcon™ cultureslides) at a concentration of $2 \times 10^5$ cells/ml. The cells were cultured using 1 ml/chamber of a complete medium of DMEM (Hyclone, USA) under the conditions of 37° C. and 5% $CO_2$. The complete medium composition was obtained by adding 4.00 mM of L-glutamine and 4500 mg/L of glucose, sodium pyruvate and fetal bovine serum (Hyclone, USA) to 500 ml of Dulbeccos Modified Eagles Medium (pH 7.4) to a final concentration of 10%. After 15 hours of cell culture, the culture medium in the chamber was removed and replaced with 1 ml of OPTI-MEM (GIBCO, USA), and then the cells were treated with 1000 nM of SAMiRNA-FITC under a light-shielded condition at indicated time points (0 hr, 0.5 hr, 1 hr, 3 hr and 12 hr) such that IFA (ImmunoFluorescence Assay) could be performed at the same time.

6.2: Immunofluorescence Assay (IFA) for Confocal Microscopy

An IFA was performed under a light-shielded condition. The cell culture medium treated with SAMiRNA-FITC was removed from the 2-chamber polystyrene vessel by a 1000 p pipettor, and then the cells were washed twice with 1 ml of OPTI-MEM. Next, the cells were washed once with 1 ml of 1×PBS for 3 minutes, and then treated with 500 ul of 2% PFA (paraformaldehyde) and fixed at room temperature for 30 minutes. The 2% PFA used herein was prepared freshly, filtered and then freeze dried. After cell fixation, the cells were washed twice with 1 ml of 1×PBS for 3 minutes each time, and then treated with 500 ul of a blocking solution containing 0.1% Triton X-100 (USB) and 10% BSA (Albumin, Bovine, pH 7.0) in 1×PBS, after which the cells were blocked at room temperature for 30 minutes, and then briefly washed once with 1×PBS after removal of the blocking solution. Next, primary antibody (EEA1(H-300), Santa Cruz, sc-33585) for staining intracellular endosomes was diluted at a ratio of 500:1 (v/v) in a solution containing 0.1% Triton X-100 (USB) and 3% BSA (Albumin, Bovine, pH 7.0) in 1×PBS, after which the cells were treated 500 ul of the antibody dilution and covered with a foil for 90 minutes, thereby performing primary staining. After primary staining, the cells were washed three times with 1 ml of 1×PBS for 3 times each time. Secondary antibody (Alexa Fluor 546 Goat anti-mouse IgG (H+L), Invitrogen Molecular Probes) showing red fluorescence was diluted at a ratio of 1000:1 in a solution containing 0.1% Triton X-100 (USB) and 3% BSA (Albumin, Bovine, pH7.0) in 1×PBS, and then the cells were treated with 500 ul of the secondary antibody dilution and covered with a foil for 90 minutes, thereby performing secondary staining. After secondary staining, the cells were washed three times with 1 ml of 1×PBS for 3 minutes each time, and 500 ul of a 1000:1 (v/v) dilution of DAPI (DAPI, Dilactate, Sigma, D-9564), 10 mg/ml in D.W) in 1×PBS was added to the cells, and the nucleus was stained at room temperature for 20 minutes. Next, the cells were washed three times with 1 ml of 1×PBS for 3 minutes each time, and the chamber wall was detached, and then one drop of mounting medium (IMMU-MOUNT, Thermo Scientific Shandon, cat. NO. 9990402) was dropped on the cells while preventing the entry of air bubbles. Next, the cells were carefully covered with a cover glass, and dried under a light-shield condition using a foil at room temperature for 20 minutes or more until the mounting medium would be hardened. Next, the cells were observed by detecting FITC signal (green) and Alexa546 (red) signal using a confocal microscope (LSM700, Carl Zeiss), followed by image data analysis.

6.3: Analysis of Mono-HEG-SAMiRNA-FITC Image Data by Confocal Microscope

Using a confocal microscope, 2D images at 400× magnification were acquired at varying time points (0 hr, 0.5 hr, 1 hr, 3 hr, and 12 hr), and 3D images of the cells were obtained by z-stacking at 1000× magnification. The 2D and 3D images were analyzed to determine whether the merge of the FITC signal and the Alexa546 signal occurred (co-localization of SAMiRNA-FITC nanoparticles to endosomes) and whether the FITC signal was located in the intracellular cytoplasm. The images obtained by the confocal microscope were analyzed by ZEN 2009 light edition (Carl Zeiss) software.

As a result, it was shown that, in the case of amine-Mono-HEG-SAMiRNA comprising an amine group, the FITC signal that appeared as large spots in the initial stage appeared as small spots with the passage of time after treatment, and the amine-Mono-HEG-SAMiRNA was present in the cytoplasm in a larger amount than Mono-HEG-SAMiRNA (FIG. 18).

6.4: Quantitative Analysis of FITC Fluorescence Value of Cells at Varying Time Points by Densitometer Software At early time points (0 min, 15 min, 30 min, and 60 min) after treatment with FITC-labeled SAMiRNA, 6-cut 2D images were obtained at 200× magnification using a confocal microscope, and then the FITC fluorescence value of each image at each time point was quantified using Image J densitometer software, thereby comparatively analyzing the delivery efficiency of SAMiRNA-FITC at each time point between the presence and absence of the amine group. As a result, it could be seen that the time-dependent fluorescence value of amine-Mono-HEG-SAMiRNA was higher than that of Mono-HEG-SAMiRNA (FIG. 19). The above experimental results suggest that the introduction of the amine group can further increase the intracellular delivery efficiency of Mono-HEG-SAMiRNA.

6.5: Comparative Experiment on the Universal Ability of Modified Amine-Mono-HEG-SAMiRNA-DN Combi to Inhibit Dengue Virus Replication Mono-HEG-SAMiRNA-DN Combi, a new type of therapeutic agent, was synthesized by introducing an amine group into Combi-SAMiRNA, and was subjected to a screening experiment at a concentration of 500 nM in order to confirm whether it has a significant difference from Combi-SAMiRNA with respect to the ability to inhibit the replication of each dengue virus serotype.

The invention claimed is:

1. A double-stranded oligo RNA structure having a structure represented by the following structural formula (1) to form a nanoparticle:

A-X—R—Y—B    Structural formula (1)

wherein A represents a hydrophilic compound, B represents a hydrophobic compound, X and Y each independently represents a simple covalent bond or a linker-mediated covalent bond, and R represents a dengue virus-specific siRNA comprising a sense strand of SEQ ID NO:71 and an antisense strand of a sequence complementary thereto, wherein the hydrophobic compound is located in the center of the n (1) to (3), and the linker J is selected from the group consisting of $PO_3^-$, $SO_3$ and $CO_2$:

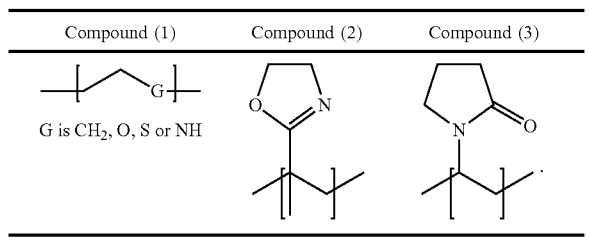

7. The double-stranded oligo RNA structure of claim 1, wherein the hydrophobic compound has a molecular weight of 250-1,000.

8. The double-stranded oligo RNA structure of claim 7, wherein the hydrophobic compound is selected from the group consisting of a steroid derivative, a glyceride derivative, glycerol ether, polypropylene glycol, a $C_{12}$-$C_{50}$ unsaturated or saturated hydrocarbon, diacylphosphatidylcholine, fatty acid, phospholipid, lipopolyamine.

9. The double-stranded oligo RNA structure of claim 8, wherein the steroid derivative is selected from the group consisting of cholesterol, cholestanol, cholic acid, cholesteryl formate, cholestanyl formate, and cholesteryl amine.

10. The double-stranded oligo RNA structure of claim 8, wherein the glyceride derivative is selected from mono-, di-, and tri-glycerides.

11. The double-stranded oligo RNA structure of claim 1, wherein the covalent bond represented by X and Y is either a non-degradable bond or a degradable bond.

12. The double-stranded oligo RNA structure of claim 11, wherein the non-degradable bond is either an amide bond or a phosphate bond.

13. The double-stranded oligo RNA structure of claim 11, wherein the degradable bond is any one selected from the group consisting of a disulfide bond, an acid-degradable bond, an ester bond, an anhydride bond, a biodegradable bond, and an enzyme-degradable bond.

14. The double-stranded oligo RNA structure of claim 1, wherein a ligand having the property of binding specifically to a receptor that enhances target cell internalization by receptor-mediated endocytosis (RME) is further bound to the hydrophilic compound.

15. The double-stranded oligo RNA structure of claim 14, wherein the ligand is selected from the group consisting of target receptor-specific antibodies, aptamer, peptide, folate, N-acetyl galactosamine (NAG), glucose, and mannose.

16. The double-stranded oligo RNA structure of claim 1, wherein an amine or polyhistidine group is additionally introduced into the distal end of the hydrophilic compound bound to the siRNA.

17. The double-stranded oligo RNA structure of claim 16, wherein the amine or polyhistidine group is connected to the hydrophilic compound or the hydrophilic block by one or more linkers.

18. The double-stranded oligo RNA structure of claim 16, wherein the amine group is any one selected from primary, secondary and tertiary amine groups.

19. The double-stranded oligo RNA structure of claim 16, wherein the polyhistidine group comprises 3 to 10 histidines.

20. Nanoparticles comprising the double-stranded oligo RNA structure of claim 1.

21. Nanoparticles of claim 20, wherein the nanoparticles are composed of a double-stranded oligo RNA structure comprising siRNAs having different sequences.

* * * * *